US006815437B1

(12) United States Patent
Commerçon et al.

(10) Patent No.: US 6,815,437 B1
(45) Date of Patent: Nov. 9, 2004

(54) STREPTOGRAMINES, THEIR PREPARATION AND COMPOSITIONS CONTAINING THEM

(75) Inventors: Alain Commerçon, Vitry-sur-Seine (FR); Hervé Bouchard, Thiais (FR); Yves Ribeill, Raleigh, NC (US); Eric Bacque, Morsang sur Orge (FR); Baptiste Ronan, Clamart (FR); Jean-Claude Barriere, Bures sur Yvette (FR); Gérard Puchault, Marcilly (FR); Corinne Terrier, Livry Gargan (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/492,392

(22) Filed: Jan. 27, 2000

Related U.S. Application Data

(63) Continuation of application No. PCT/FR98/01639, filed on Jul. 24, 1998.

(30) Foreign Application Priority Data

Jul. 28, 1997 (FR) ............................................ 97 09557

(51) Int. Cl.$^7$ .............................................. A61K 31/33
(52) U.S. Cl. ...................... 514/183; 514/11; 530/317
(58) Field of Search .................... 514/183, 11; 530/317; 517/11

(56) References Cited

U.S. PATENT DOCUMENTS

| 4,590,004 A | 5/1986 | Corbet et al. ............... 530/317 |
| 4,668,669 A | 5/1987 | Barriere et al. ............. 514/183 |
| 4,798,827 A | 1/1989 | Barriere et al. ............. 514/183 |
| 4,866,172 A | 9/1989 | Chatterjee et al. .......... 540/456 |
| 5,326,782 A | 7/1994 | Barriere et al. ............. 514/411 |
| 5,637,565 A | 6/1997 | Anger et al. ................... 514/11 |
| 5,726,151 A | 3/1998 | Anger et al. ................... 514/11 |
| 5,891,695 A | 4/1999 | Blanc et al. ................. 435/183 |

FOREIGN PATENT DOCUMENTS

| FR | 2 549 065 A1 | 1/1985 |
| GB | 2 206 879 A | 1/1989 |

OTHER PUBLICATIONS

Ludbrook (Clinical and Experimental Pharmacology and Physiology 28 (5–6) 488–92, 2001).*
Bryant (Pediatric Allergy and Immunology 9 (3) 108–15, 1998).*
Bezeau (Journal of Clinical and Experimental Neuropsychology 23 (3) 399–406, 2001).*
Bolton (Journal of Clinical Pharmacology 38 (5) 408–12, 1998).*
Willenheimer (Progress in Cardiovascular Diseases 44 (3) 155–67, 2001).*
Chung (Plastic and Reconstructive Surgery 109 (1) 1–6, 2002).*
Atkinson (Chronobiology International 18 (6) 1041–53, 2001).*
Gavini, Archiv der Pharmazie 333 (10) 341_6, 2000.*
Fudou, Journal of Antibiotics 54 (2) 149–52, 2001.*
Juvvadi Journal Journal of Peptide Research 53 (3) 244–51, 1999.*
Avrahami, Biochemistry 40 (42) 12591–603, 2001.*
Otvos, Protein Science 9 (4) 742–9, 2000.*
J.C. Barrière, et al., "Recent Developments in Streptogramin Research," *Current Pharmaceutical Design*, 1998, 4, pp. 155–180.
Certified English Translation of article by Preud'Homme et al., "Pristinamycin: Isolation, Characterization and Identification of the Constituents," Bulletin de la Societe Chimique de France, No. 2, pp. 585–591 (1968).

* cited by examiner

*Primary Examiner*—Robert A. Wax
*Assistant Examiner*—David Lukton
(74) *Attorney, Agent, or Firm*—Finnegan, Henderson, Farabow, Garrett & Dunner, L.L.P.

(57) ABSTRACT

Group A streptogramin derivatives of formula (I):

(I)

the salts thereof, and mixtures of stereoisomers thereof, as well as processes for preparing them and pharmaceutical compositions comprising them are disclosed.

17 Claims, No Drawings

STREPTOGRAMINES, THEIR PREPARATION AND COMPOSITIONS CONTAINING THEM

This application is a continuation of International Application No. PCT/FR98/01639, filed Jul. 24, 1998, the content of which is incorporated herein by reference.

The present invention relates to group A steptogramin derivatives of general formula:

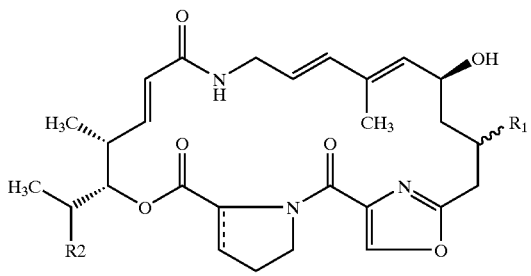

in which

R$_1$ is a radical —NR'R" for which R' is a hydrogen atom or a methyl radical, and R" is a hydrogen atom or an alkyl, cycloalkyl, allyl, propynyl, benzyl or —OR'" radical, R'" being a hydrogen atom or an alkyl, cycloalkyl, allyl, propynyl or benzyl radical, or R" represents —NR$_3$R$_4$, it being possible for R$_3$ and R$_4$ to represent a methyl radical, or to form together with the nitrogen atom to which they are attached a saturated or unsaturated 4- or 5-membered heterocycle which may, in addition, contain another heteroatom chosen from nitrogen, oxygen or sulphur, R$_2$ is a hydrogen atom or a methyl or ethyl radical, and the bond === represents a single bond or a double bond, as well as their salts, which exhibit a particularly advantageous antibacterial activity and a good degree of metabolic stability.

Among the known streptogramins, pristinamycin (RP 7293), an antibacterial of natural origin produced by *Streptomyces pristinaespiralis* was first isolated in 1955. The pristinamycin marketed under the name Pyrostacine[7] consists mainly of pristinamycin II$_A$ combined with pristinamycin I$_A$.

Another antibacterial of the class of streptogramins: virginiamycin, has been prepared from *Streptomyces virginiae*, ATCC 13161 [Antibiotics and Chemotherapy, 5; 632 (1955)]. Virginiamycin (Staphylomycine[7]) consists mainly of factor M$_1$ combined with factor S.

Semisynthetic derivatives of streptogramins of structure:

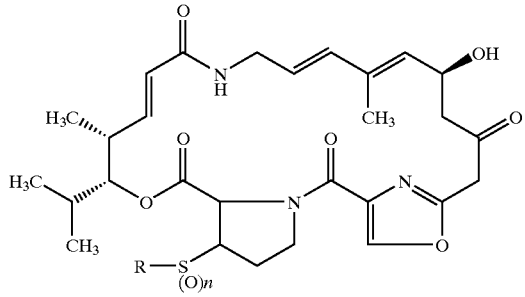

for which n is 0 to 2 have been described in patents EP 135410 and EP 191662. Combined with a semisynthetic component of group B streptogramins they manifest a synergistic action and can be used by the injection route.

In general formula (I), unless otherwise stated, the alkyl radicals are straight or branched and contain 1 to 6 carbon atoms; the cycloalkyl radicals contain 3 to 4 carbon atoms; the chain ‐‐‐ at the 16-position means: when R" is other than —OR'" or —NR$_3$R$_4$, the R epimer or mixtures of the R and S epimers in which the R epimer is predominant, and when R" is —OR'" or —NR$_3$R$_4$, the R and S epimers and mixtures thereof.

When R" is a radical —NR$_3$R$_4$ for which R$_3$ and R$_4$ form together with the nitrogen atom to which they are attached a saturated or unsaturated 4- or 5-membered heterocycle, the latter may be in particular azetidine, azolidine or imidazolyl.

The streptogramin derivatives of general formula (I) may be prepared from the components of the natural pristinamycin of general formula:

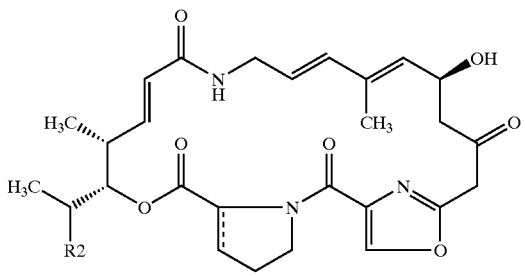

in which R$_2$ is as defined above, by the action of an amine of general formula:

$$H_2N—R"$$ (III)

in which R" is as defined above, followed by the action of an agent for reducing the intermediate enamine (or oxime) obtained, and then, when it is desired to obtain a streptogramin derivative of general formula (I) for which R' is a methyl radical, followed by a second reductive amination, by the action of formaldehyde or of a derivative generating formaldehyde in situ and the reduction of the intermediate enamine.

The action of the amine is generally carried out in an organic solvent such as an alcohol (for example methanol or ethanol), a chlorinated solvent (for example dichloromethane, dichloroethane or chloroform), a nitrile (for example acetonitrile), or pyridine, at a temperature of between 0 and 30 EC, and optionally in the presence of a dehydrating agent such as, for example, magnesium sulphate, sodium sulphate or molecular sieves. Preferably, the procedure is carried out under an inert atmosphere (for example argon). It is also possible to cause the amine salt to react. Preferably, to prepare derivatives for which the bond === represents a double bond, the procedure is carried out in an organic solvent such as a nitrile (for example acetonitrile) in the presence of an acid, such as an organic acid (for example acetic acid); in this case, the addition of a dehydrating agent is not necessary. When a streptogramin derivative of general formula (I) for which R" is a radical —OR'" is prepared, it is possible to isolate the intermediate oxime of general formula:

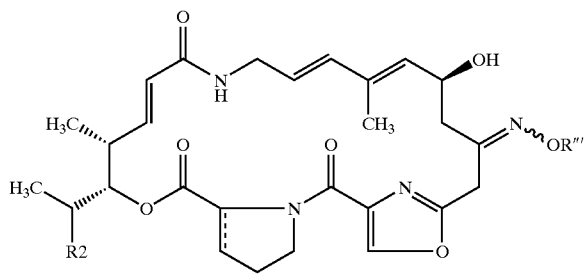

(IV)

in which R$_2$ and R''' are as defined above, and then to reduce this product to a derivative of general formula (I) for which R' is a hydrogen atom, and optionally use it in the subsequent reductive amination operation.

The reduction is carried out by the action of a reducing agent, for example an alkali metal borohydride (for example sodium cyanoborohydride or triacetoxyborohydride) in the presence of an organic acid (for example acetic acid) in an organic solvent as mentioned above for the amination reaction.

Where appropriate, the subsequent reductive amination operation, intended to obtain the disubstituted amine, is carried out under similar conditions.

According to the invention, the streptogramin derivatives of general formula (I) may also be prepared by the action of the ketone corresponding to the desired R'' radical on the amine-containing derivative of general formula:

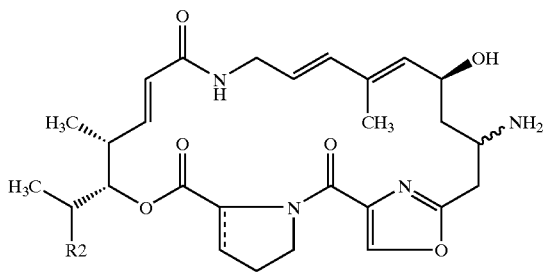

(V)

in which R$_2$ is as defined above, followed, when it is desired to obtain a streptogramin derivative of general formula (I) for which R' is a methyl radical, by a second reductive amination, by the action of formaldehyde or of a derivative generating formaldehyde in situ and the reduction of the intermediate enamine.

The reaction is carried out under conditions similar to those described above.

The amine of general formula (I) may be prepared as described above, from a streptogramin derivative of general formula (II).

The pristinamycin derivatives of general formula (II) correspond respectively-to pristinamycin II$_A$ (PII$_A$), to pristinamycin II$_B$ (PII$_B$), to pristinamycin II$_C$ (PII$_C$), to pristinamycin II$_D$ (PII$_D$), to pristinamycin II$_F$ (PII$_F$), and to pristinamycin II$_G$ (PII$_G$), which are known components of natural pristinamycin. The components PII$_F$ and PII$_G$ have been described in European patent application EP 614910.

Pristinamycin II$_C$ (PII$_C$) and pristinamycin II$_D$ (PII$_D$) may be obtained as described by J. C. Barrière et al., Expert. Opin. Invest. Drugs, 3(2), 115–31 (1994).

The preparation and separation of the components of the natural group A streptogramins [streptogramins of general formula (II)] is carried out by fermentation and isolation of the constituents from the fermentation broth according to or by analogy with the method described by J. Preud'homme et al., Bull. Soc. Chim. Fr., vol. 2, 585 (1968).

Alternatively, the preparation of the natural components of group A may be carried out by specific fermentation, as described in patent application FR 2,689,518.

The streptogramin derivatives of general formula (I) may be purified, where appropriate, by physical methods such as crystallization or chromatography.

The derivatives of general formula (I) may in particular be obtained in the form of the 16R epimer. The separation of the 16R epimer form and the 16S epimer form may be carried out by flash chromatography, by high-performance liquid chromatography (HPLC) or by centrifugal partition chromatography (CPC), from the mixture of the 16R and 16S epimers.

The streptogramin derivatives of general formula (I) may be converted to the state of addition salts with acids, by known methods. It is understood that these salts are also included within the scope of the present invention.

As examples of addition salts with pharmaceutically acceptable acids, there may be mentioned the salts formed with inorganic acids (hydrochlorides, hydrobromides, sulphates, nitrates, sulphates) or with organic acids (succinates, fumarates, tartrates, acetates, propionates, maleates, citrates, methanesulphonates, ethanesulphonates, phenylsulphonates, p-toluenesulphonates, isethionates, naphthylsulphonates or camphorsulphonates, or with the substitution derivatives of these compounds).

The streptogramin derivatives according to the present invention have antibacterial properties and properties synergizing the antibacterial activity of the group B streptogramin derivatives. They are particularly advantageous because of their activity, alone or combined, as well as because of their enhanced metabolic stability compared with the previously known group A derivatives.

When they are combined with a component or a derivative of the group B streptogramins, they may be chosen, depending on whether it is desired to obtain an orally or parenterally administrable form, from the natural components: pristinamycin I$_A$, pristinamycin I$_B$, pristinamycin I$_C$, pristinamycin I$_D$, pristinamycin I$_E$, pristinamycin I$_F$, pristinamycin I$_G$, virginiamycin S$_1$, S$_3$ or S$_4$, vernamycin B or C, etamycin or from the semisynthetic derivatives as described in patents or patent applications U.S. Pat. Nos. 4,618,599, 4,798,827, 5,326,782, EP 772630 or EP 770132, in particular the streptogramin derivatives of general formula:

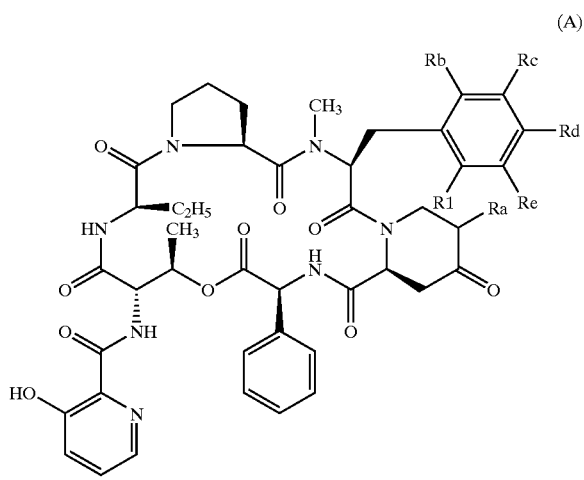

(A)

in which,
1. Rb, Rc, Re and Rf are hydrogen atoms, Rd is a hydrogen atom or a dimethylamino radical, and Ra is a radical of structure —CH$_2$R'a for which R'a is 3-pyrrolidinylthio or 3- or 4-piperidylthio which may be substituted with alkyl, or alkylthio substituted with 1 or 2 hydroxysulphonyl, alkylamino, dialkylamino (itself optionally substituted with mercapto or dialkylamino), or substituted with 1 or 2 optionally substituted piperazine rings, morpholino, thiomorpholino, piperidino, 1-pyrrolidinyl, 2-, 3- or 4-piperidyl or 2- or 3-pyrrolidinyl (which may be substituted with alkyl), or alternatively Ra is a radical of structure =CHR'a for which R'a is 3-pyrrolidinylamino, 3- or 4-piperidylamino, 3-pyrrolidinyloxy, 3- or 4-piperidyloxy, 3-pyrrolidinylthio, 3- or 4-piperidylthio which may be substituted with alkyl, or R'a is alkylamino, alkyloxy or alkylthio substituted with 1 or 2 hydroxysulphonyl, alkylamino, dialkylamino (itself optionally substituted with dialkylamino), or with trialkylammonio, 4- or 5-imidazolyl, or with 1 or 2 optionally substituted piperazine rings, morpholino, thiomorpholino, piperidino, 1-pyrrolidinyl, 2-, 3- or 4-piperidyl or 2- or 3-pyrrolidinyl (which may be substituted with alkyl), or Ra is a 3- or 4-quinuclidinylthiomethyl radical, or alternatively
2. Ra is a hydrogen atom and
a) either Rb, Re and Rf are hydrogen atoms, Rd is a radical —NHCH$_3$ or —N(CH$_3$)$_2$ and Rc is a chlorine or bromine atom, or represents an alkenyl radical containing 3 to 5 carbon atoms [if Rd is —N(CH$_3$)$_2$],
b) or Rb, Rd, Re and Rf represent a hydrogen atom and Rc is a halogen, or an aminomonoalkyl, aminodialkyl, alkyloxy, trifluoromethoxy, thioalkyl, C$_1$ to C$_3$ alkyl or trihalomethyl radical,
c) or Rb, Rc, Re and Rf represent a hydrogen atom and Rd is a halogen, or an ethylamino, diethylamino or methylethylamino, alkyloxy or trifluoromethyloxy, thioalkyl, C$_1$ to C$_6$ alkyl, aryl or trihalomethyl radical,
d) or Rb, Re and Rf represent a hydrogen atom and Rc is halogen or an aminomonoalkyl or aminodialkyl, alkyloxy or trifluoromethyloxy, thioalkyl or C$_1$ to C$_3$ alkyl radical, and Rd is halogen or an amino, aminomonoalkyl or aminodialkyl, alkyloxy or trifluoromethyloxy, thioalkyl, C$_1$ to C$_6$ alkyl or trihalomethyl radical,
e) or Rc, Re and Rf represent a hydrogen atom and Rb and Rd represent a methyl radical.
It is understood that the combinations of the derivatives according to the invention and of the group B streptogramins are also included within the scope of the present invention.

In vivo, on experimental infections of mice with Staphylococcus aureus IP 8203 at doses of between 25 and 150 mg/kg orally and/or subcutaneously (CD$_{50}$), they synergize the antimicrobial activity of pristinamycin I$_B$ of prostinamycin I$_A$ or of quinupristin (30/70 combination).

Finally, the products according to the invention are particularly advantageous because of their low toxicity. None of the products exhibited toxicity at doses of 300 mg/kg or greater than 300 mg/kg by the subcutaneous route.

Of particular interest are the products of general formula (I) for which R$_1$ is a radical —NR'R" for which R' is a hydrogen atom or a methyl radical, and R" is a hydrogen atom, an alkyl, cycloalkyl, allyl, propynyl, benzyl or —OR'" radical, R'" being an alkyl radical containing 1 to 6 carbon atoms, an allyl or propynyl radical, or R" represents —NR$_3$R$_4$, it being possible for R$_3$ and R$_4$ to represent a methyl radical, or to form together with the nitrogen atom to which they are attached a saturated or unsaturated 4- or 5-membered heterocycle which may, in addition, contain another heteroatom chosen from nitrogen, oxygen or sulphur, R$_2$ is a hydrogen atom or a methyl or ethyl radical, and the bond ==== represents a single bond or a double bond, as well as their salts and in which the chain ～w～ at the 16-position means: when R" is other than —OR'" or —NR$_3$R$_4$, the R epimer or mixtures of the R and S epimers in which the R epimer is predominant, and when R" is —OR'" or —NR$_3$R$_4$, the R and S epimers and mixtures thereof; and among these products, most particularly the derivatives of general formula (I) for which R$_1$ is a radical —NR'R" for which R' is a hydrogen atom or a methyl radical, and R" is a hydrogen atom, an alkyl radical containing 1 to 4 carbon atoms, a cycloalkyl, allyl, propynyl, benzyl or —OR'" radical, R'" being an alkyl radical containing 1 to 3 carbon atoms, or an allyl or propynyl radical, or R" represents —NR$_3$R$_4$, it being possible for R$_3$ and R$_4$ to form together with the nitrogen atom to which they are attached a 5-membered saturated heterocycle, R$_2$ is a methyl or ethyl radical, and the bond ==== represents a single bond or a double bond, as well as their salts and in which the chain ～w～ at the 16-position is as defined above.

More especially, among these products, the following derivatives are of great interest:
(16R)-16-dimethylamino-16-deoxopristinamycin II$_A$;
(16R)-16-methoxyamino-16-deoxopristinamycin II$_B$;
(16R)-16-ethoxyamino-16-deoxopristinamycin II$_B$;
(16R)-16-allyloxyamino-16-deoxopristinamycin II$_B$;.
(16R)-16-methoxyamino-16-deoxopristinamycin II$_A$.

The following examples, given with no limitation being applied, illustrate the present invention.

In the examples which follow, the 16-deoxopristinamycin II$_A$ (or II$_B$) nomenclature means the replacement of the ketone function at the 16-position with 2 hydrogen atoms.

EXAMPLE 1

(16R)-16-Benzylamino-16-deoxopristinamycin II$_B$ 3 g of magnesium sulphate and 0.328 cm$^3$ of benzylamine are added at about 20 EC, under an argon atmosphere, to 1.06 g of pristinamycin II$_B$ in solution in 15 cm$^3$ of methanol. After stirring for 24 hours, 0.151 g of sodium cyanoborohydride and 0.5 cm$^3$ of acetic acid are added. The reaction mixture is stirred for 1 hour and then filtered on Celite. The Celite is washed with 100 cm$^3$ of methanol, the filtrate is concentrated under reduced pressure (2.7 kPa) to give a residue which is diluted in 200 cm$^3$ of dichloromethane. The organic phase is washed with twice 100 cm$^3$ of a 5% aqueous sodium hydrogen carbonate solution. The organic phase is decanted off and the aqueous phase is taken up in twice 50 cm³ of dichloromethane. The organic phases are combined, dried over magnesium sulphate, filtered and then concentrated to dryness under reduced pressure (2.7 kPa) to give 1.3 g of a residue which is purified by flash chromatography (eluent: dichloromethane-methanol-acetonitrile (84-8-8 by volume)). 0.424 g of a mixture of the (16R)/(16S) isomers=65/35 of 16-benzylamino-16-deoxopristinamycin II$_B$, in the form of a yellow powder, and 0.144 g of the mixture of the (16R)/(16S) isomers>95/5 of 16-benzylamino-16-deoxopristinamycin II$_B$, in the form of a yellow powder, are thus obtained. Each of these mixtures is purified by HPLC [C18 column (15–20 μm), (λ=254 nm), eluent: acetonitrile-water (80–20 by volume)] to give, in total, 0.250 g of (16R)-16-benzylamino-16-deoxopristinamycin II$_B$ in the form of a pale yellow powder melting at around 130 EC (dec.).

¹H NMR spectrum (400 MHz, CDCl₃, δ in ppm): 0.95 and 1.00 (2 d, J=6.5 Hz, 3H each: CH₃ at position 30 and CH₃ at position 31); 1.08 (d, J=6.5 Hz, 3H: CH₃ at position 32); 1.43 (mt, 1H: 1H of CH₂ at position 15); 1.68 (s, 3H: CH₃ at position 33); from 1.70 to 2.00 (mt, 5H: 1H of CH₂ at position 15—CH₂ at position 25—1H of CH₂ at position 26 and CH at position 29); 2.12 (mt, 1H: 1H of CH₂ at position 26); from 2.65 to 2.80 (mt, 1H: CH at position 4); 2.78 and 3.18 (2 dd, respectively J=16 and 8 Hz and J=16 and 4 Hz, 1H each: CH₂ at position 17); 3.25 (mt, 1H: CH at position 16); 3.47 (mt, 1H: 1H of CH₂ at position 9); 3.80 (mt, 1H: 1H of CH₂ at position 24); 3.81 and 4.02 (2 d, J=14 Hz, 1H each: CH₂N); 3.96 (mt, 1H: 1H of CH₂ at position 24); 4.38 (mt, 1H: 1H of CH₂ at position 9); 4.66 (mt, 1H: CH at position 14); from 4.70 to 4.80 (mt, 2H: CH at position 3 and CH at position 27); 5.36 (d, J=9 Hz, 1H: CH at position 13); 5.64 (mt, 1H: CH at position 10); 5.78 (dd, J=16 and 2 Hz, 1H: CH at position 6); 6.00 (mt, 1H: CONH); 6.14 (d, J=16 Hz, 1H: CH at position 11); 6.50 (dd, J=16 and 5 Hz, 1H: CH at position 5); from 7.25 to 7.40 (mt, 5H; aromatic H of benzyl); 8.09 (s, 1H: CH at position 20).

EXAMPLE 2

(16R)-16-Cyclopropylamino-16-deoxopristinamycin II$_B$ 9 g of magnesium sulphate and 0.6 cm³ of cyclopropylamine are added at about 20 EC, under an argon atmosphere, to 3 g of pristinamycin II$_B$ in solution in 30 cm³ of methanol. After stirring for 17 hours 30 minutes, 0.43 g of sodium cyanoborohydride is added and then, after 30 minutes, 0.5 cm³ of acetic acid. The reaction mixture is stirred for 2 hours and then filtered on Celite. The Celite is washed with methanol and then the filtrate is concentrated under reduced pressure (2.7 kPa) to give 4.64 g of a yellow foam which is dissolved in 100 cm³ of ethyl acetate and 5 cm³ of methanol and then washed with 3 times 25 cm³ of distilled water. The organic phases are combined, dried over magnesium sulphate, filtered and then concentrated under reduced pressure (2.7 kPa) to give 2.2 g of a yellow foam which is purified by flash chromatography [eluent: dichloromethane-methanol-acetonitrile (84-8-8 by volume)]. 0.61 g of a yellow powder is isolated which is stirred in 15 cm³ of ethyl ether, filtered and then dried under reduced pressure (2.7 kPa), at 30 EC, to give 0.508 g of (16R)-16-cyclopropylamino-16-deoxopristinamycin II$_B$ in the form of a cream-coloured powder melting at around 135 EC (dec.).

¹H NMR spectrum (400 MHz, CDCl₃, δ in ppm): 0.35 to 0.60 (mt, 4H: CH₂ of cyclopropyl); 0.97 and 1.00 (2 d, J=6.5 Hz, 3H each: CH₃ at position 30 and CH₃ at position 31); 1.08 (d, J=6.5 Hz, 3H: CH₃ at position 32); 1.33 (mt, 1H: 1H of CH₂ at position 15); from 1.70 to 2.00 (mt, 5H: 1H of CH₂ at position 15—CH₂ at position 25—1H of CH₂ at position 26 and CH at position 29); 1.77 (s, 3H: CH₃ at position 33); 2.13 (mt, 1H: 1H of CH₂ at position 26); 2.29 (mt, 1H: CH of cyclopropyl); 2.74 (mt, 1H: CH at position 4) 2.82 and 3.25 (2 dd, respectively J=16 and 8 Hz and J=16 and 4 Hz, 1H each: CH₂ at position 17); 3.33 (mt, 1H: CH at position 16); 3.51 (mt, 1H: 1H of CH₂ at position 9); 3.83 and 3.99 (2 mts, 1H each: CH₂ at position 24); 4.35 (mt, 1H: 1H of CH₂ at position 9); 4.65 (mt, 1H: CH at position 14); from 4.70 to 4.80 (mt, 2H: CH at position 3 and CH at position 27); 5.39 (d, J=9 Hz, 1H: CH at position 13); 5.65 (mt, 1H: CH at position 10); 5.79 (dd, J=17 and 2 Hz, 1H: CH at position 6); 5.97 (mt, 1H: CONH); 6.17 (d, J=16 Hz, 1H: CH at position 11); 6.53 (dd, J=17 and 5 Hz, 1H: CH at position 5); 8.12 (s, 1H: CH at position 20).

EXAMPLE 3

(16R)-16-Allylamino-16-deoxopristinamycin II$_B$

By carrying out the procedure in a manner similar to that described in Example 1, but starting with 5 g of pristinamycin II$_B$ in solution in 70 cm³ of methanol, 15 g of magnesium sulphate and 1.45 cm³ of allylamine and after adding at 24 hours [lacuna] 0.714 g of sodium cyanoborohydride and 5 cm³ of acetic acid, a solid is obtained after stirring for a further 1 hour and after treatment, which solid is purified by flash chromatography [eluent: dichloromethane-methanol (95-5 by volume)] to give 0.975 g of (16R)-16-allylamino-16-deoxopristinamycin II$_B$ in the form of a pale yellow powder melting at around 122–124 EC.

¹H NMR spectrum (400 MHz, CDCl₃, δ in ppm): 0.96 and 1.00 (2 d, J=6.5 Hz, 3H each: CH₃ at position 30 and CH₃ at position 31); 1.08 (d, J=6.5 Hz, 3H: CH₃ at position 32); 1.38 (mt, 1H: 1H of CH₂ at position 15); from 1.65 to 2.00 (mt, 5H: 1H of CH₂ at position 15—CH₂ at position 25—1H of CH₂ at position 26 and CH at position 29); 1.77 (s, 3H: CH₃ at position 33); 2.12 (mt, 1H: 1H of CH₂ at position 26); from 2.70 to 2.80 (mt, 1H: CH at position 4); 2.74 and 3.13 (2 dd, respectively J=16 and 8 Hz and J=16 and 5 Hz, 1H each: CH₂ at position 17); from 3.20 to 3.35 (mt, 2H: CH at position 16 and 1H of CH₂N); from 3.45 to 3.55 (mt, 2H: 1H of CH₂ at position 9 and 1H of CH₂N); 3.83 and 3.98 (2 mts, 1H each: CH₂ at position 24); 4.38 (mt, 1H: 1H of CH₂ at position 9); 4.70 (mt, 1H: CH at position 14); from 4.65 to 4.80 (mt, 2H: CH at position 3 and CH at position 27); 5.15 and 5.24 (2 dd, respectively J=10 and 1.5 Hz and J=18 and 1.5 Hz, 1H each: =CH₂ of allyl); 5.40 (d, J=9 Hz, 1H: CH at position 13); 5.66 (mt, 1H: CH at position 10) 5.80 (dd, J=17 and 2.5 Hz, 1H: CH at position 6) from 5.85 to 6.00 (mt, 2H: CH= of allyl and CONH) 6.16 (d, J=16 Hz, 1H: CH at position 11); 6.52 (dd, J=17 and 5 Hz, 1H: CH at position 5); 8.10 (s, 1H: CH at position 20).

EXAMPLE 4

(16R)-16-Propyn-2-ylamino-16-deoxopristinamycin II$_B$

By carrying out the procedure in a manner similar to that described in Example 1, but starting with 5 g of pristinamycin II$_B$ in solution in 70 cm³ of methanol, 10 g of magnesium sulphate and 1.3 cm³ of propargylamine and after adding at 22 hours [lacuna] 0.714 g of sodium cyanoborohydride and 5 cm³ of acetic acid, 5.5 g of a solid are obtained after stirring for a further 3 hours 30 min and after treatment, which solid is purified by flash chromatography [eluent: dichloromethane-methanol (96-4 by volume)] to [lacuna] 0.266 g of (16R)-16-propyn-2-ylamino-16-deoxopristinamycin II$_B$ in the form of an ochre-coloured powder melting at around 124 EC (dec.).

¹H NMR spectrum (400 MHz, CDCl₃, δ in ppm): 0.95 and 1.00 (2 d, J=6.5 Hz, 3H each: CH₃ at position 30 and CH₃ at position 31); 1.07 (d, J=6.5 Hz, 3H: CH₃ at position 32); 1.53 (mt, 1H: 1H of CH₂ at position 15); from 1.60 to 2.00 (mt, 5H: 1H of CH₂ at position 15—CH₂ at position 25—1H of CH₂ at position 26 and CH at position 29); 1.79 (s, 3H: CH₃ at position 33); 2.13 (mt, 1H: 1H of CH₂ at position 26); 2.26 (t, J=2 Hz, 1H: CH propynyl); from 2.70 to 2.80 (mt, 1H: CH at position 4); 2.76 and 3.16 (2 dd, respectively J=16 and 8 Hz and J=16 and 4 Hz, 1H each: CH₂ at position 17); 3.36 (mt, 1H: CH at position 16); 3.48 (mt, 1H: 1H of CH₂ at position 9); 3.56 (limiting AB, 2H: NCH₂ propynyl); 3.84 and 3.99 (2 mts, 1H each: CH₂ at position 24); 4.40 (mt, 1H: 1H of CH₂ at position 9); from 4.65 to 4.80 (mt, 3H: CH at position 3—CH at position 14 and CH at position 27) 5.36 (d, J=9 Hz, 1H: CH at position 13); 5.69 (mt, 1H: CH at position 10); 5.80 (dd, J=16 and 2 Hz, 1H: CH at position 6); 6.11 (mt, 1H: CONH); 6.17 (d, J=16 Hz, 1H: CH at position 11); 6.52 (dd, J=16 and 5 Hz, 1H: CH at position 5); 8.08 (s, 1H: CH at position 20).

EXAMPLE 5

(16R)-16-[(R)-sec-Butylamino)-16-deoxopristinamycin II$_B$

By carrying out the procedure in a manner similar to that described in Example 1, but starting with 5 g of pristinamycin II$_B$ in solution in 70 cm³ of methanol, 10 g of magnesium sulphate and 1.92 cm³ of (R)-sec-butylamine and after adding at 20 hours of stirring 0.714 g of sodium cyanoborohydride and 5 cm³ of acetic acid, 5.6 g of a solid are obtained after stirring for a further 2 hours 30 min and after treatment, which solid is purified by flash chromatography [eluent: dichloromethane-methanol (96-4 by volume)] to give 0.680 g of (16R)-16-[(R)-sec-butylamino]-16-deoxopristinamycin II$_B$ in the form of a yellow powder melting at around 156 EC (dec.).

¹H NMR spectrum (400 MHz, CDCl₃, δ in ppm): from 0.90 to 1.15 (Mt, 15H: CH₃ at position 30—CH₃ at position 31—CH₃ at position 32 and 2 CH₃ of (N-2-butyl)); 1.28 (mt, 2H: CH₂ of (N-1-methylpropyl)); 1.50 to 2.20 (mt, 7H: CH₂ at position 15—CH₂ at position 25—CH₂ at position 26 and CH at position 29); 1.79 (s, 3H: CH₃ at position 33); 2.74 (mt, 1H: CH at position 4); from 3.00 to 3.10 (mt, 2H: CH of (N-1-methylpropyl) and 1H of CH₂ at position 17); 3.25 (dd, J=16 and 4 Hz, 1H: 1H of CH₂ at position 17); from 3.50 to 3.60 (mt, 2H: 1of CH₂ at position 9 and CH at position 16); 3.80 and 3.95 (2 mts, 1H each: CH₂ at position 24); 4.28 (mt, 1H: 1H of CH₂ at position 9); from 4.70 to 4.85 (mt, 3H: CH at position 3—CH at position 4 and CH at position 27); 5.41 (d, J=9 Hz, 1H: CH at position 13); 5.68 (mt, 1H: CH at position 10); 5.80 (d, J=16 Hz, 1H: CH at position 6); from 6.10 to 6.25 (broad unresolved complex, 1H: CONH); 6.18 (d, J=16 Hz, 1H: CH at position 11); 6.55 (dd, J=17 and 5 Hz, 1H: CH at position 5); 8.11 (s, 1H: CH at position 20).

EXAMPLE 6

(16R)-16-((S)-sec-Butylaminol-16-deoxopristinamycin II$_B$

By carrying out the procedure in a manner similar to that described in Example 1, but starting with 5 g of pristinamycin II$_B$ in solution in 70 cm³ of methanol, 10 g of magnesium sulphate and 1.92 cm³ of (S)-sec-butylamine and by adding after stirring for 20 hours 0.714 g of sodium cyanoborohydride and 5 cm³ of acetic acid. The reaction mixture is stirred for 2 hours 30 min and gives, after treatment, a solid which is purified by flash chromatography [eluent: dichloromethane-methanol (96-4 by volume)]. The solid obtained is recrystallized from hot acetonitrile to give 0.590 g of (16R)-16-[(S)-sec-butylamino]-16-deoxopristinamycin II$_B$ in the form of a yellow powder melting at around 150 EC (dec.).

¹H NMR spectrum (400 MHz, CDCl₃, δ in ppm) from 0.09 to 1.15 (mt, 15H: CH₃ at position 30—CH₃ at position 31—CH₃ at position 32 and 2 CH₃ of (N-1-methylpropyl)); 1.44 (quintuplet, J=7 Hz, 2H: CH₂ of (N-1-methylpropyl)); 1.60 to 2.00 (mt, 5H: 1H of CH₂ at position 15—CH₂ at position 25—1H of CH₂ at position 26 and CH at position 29); 1.76 (s, 3H: CH₃ at position 33); 2.04 (broad d, J=14 Hz, 1H: 1H of CH₂ at position 15); 2.11 (mt, 1H: 1H of CH₂ at position 26); from 2.65 to 2.85 (mt, 1H: CH at position 4); 2.70 and 3.12 (2 dd, respectively J=16 and 11 Hz and J=16 and 4 Hz, 1H each: CH₂ at position 17); 2.80 (mt, 1H: CH of (N-1-methylpropyl)); 3.35 (mt, 1H: CH at position 16); 3.50 (mt, 1H: 1H of CH₂ at position 9); 3.81 and 3.98 (2 mts, 1H each: CH₂ at position 24); 4.33 (mt, 1H: 1H of CH₂ at position 9); from 4.65 to 4.80 (mt, 3H: CH at position 3—CH at position 14 and CH at position 27); 5.43 (d, J=9 Hz, 1H: CH at position 13); 5.62 (mt, 1H: CH at position 10); 5.78 (dd, J=16 and 2 Hz, 1H: CH at position 6); 5.86 (mt, 1H: CONH); 6.17 (d, J=16 Hz, 1H: CH at position 11); 6.53 (dd, J=17 and 5 Hz, 1H: CH at position 5); 8.12 (s, 1H: CH at position 20).

EXAMPLE 7

16-Amino-16-deoxopristinamycin II$_B$

[Mixture of the (16R)/(16S) Isomers=75/25]

200 g of magnesium sulphate, 74 g of ammonium acetate and 28 g of sodium cyanoborohydride are added at about 20 EC, under an argon atmosphere, to 100 g of pristinamycin II$_B$ in solution in 1400 cm³ of methanol. After stirring for 20 hours, the reaction mixture is filtered on Celite, and then the Celite rinsed with methanol. The filtrate is concentrated under reduced pressure (2.7 kPa) to give a chestnut-coloured oil which is divided into two equal fractions which are each diluted in 1000 cm³ of dichloromethane and then treated with a 5% aqueous sodium bicarbonate solution. The organic phases are decanted off and the aqueous phases extracted with 1000 cm³ of dichloromethane. The organic phases are combined, washed with a saturated aqueous sodium chloride solution, dried over magnesium sulphate, filtered and then concentrated to dryness under reduced pressure (2.7 kPa) to give 97.5 g of a dark yellow powder. The latter is purified by flash chromatography [eluent: dichloromethane-methanol (70–30 by volume)] to give 21.7 g of 16-amino-16-deoxopristinamycin II$_B$ (mixture of the (16R)/(16S) isomers=75/25) in the form of a beige-yellow powder.

¹H NMR spectrum [syn (16R) isomer 75% anti (16S) isomer 25%] (400 MHz, CDCl₃, δ in ppm): 0.94 and 0.98 (2d, J=6.5 Hz: CH₃ at position 30 and CH₃ at position 31 of the syn isomer); from 0.90 to 1.15 (mt: CH₃ at position 30—CH₃ at position 31 and CH₃ at position 32 of the anti isomer); 1.07 (d, J=6.5 Hz: CH₃ at position 32 of the syn isomer); 1.46 (mt: 1H of CH₂ at position 15 of the syn isomer); from 1.65 to 2.00 (mt: 1H of CH₂ at position 15 of the syn isomer—1H of CH₂ at position 15 of the anti isomer—CH₂ at position 25— 1H of CH₂ at position 26 and CH at position 29); 1.73 and 1.78 (2 s: respectively CH₃ at position 33 of the anti isomer and CH₃ at position 33 of the syn isomer); from 2.00 to 2.30, (mt: 1H of CH₂ at position 15 of the anti isomer and 1H of CH₂ at position 26); from 2.65 to 2.80 (mt: CH at position 4 and 1H of CH₂ at position 17 of the syn isomer); from 2.80 to 2.90 (mt: CH₂ at position 17 of the anti isomer); 2.95 (dd, J=16 and 5 Hz: 1H of CH₂ at position 17 of the syn isomer); from 3.30 to 3.45 (mt: 1H of CH₂ at position 9 of the anti isomer and CH at position 16 of the syn isomer); 3.48 (mt: 1H of CH₂ at position 9 of the syn isomer); 3.63 (mt: CH at position 16 of the anti isomer); 3.80 and 3.91 (2 mts: respectively CH₂ at position 24 of the anti isomer and CH₂ at position 24 of the syn isomer); 4.37 (mt: 1H of CH₂ at position 9 of the syn isomer); 4.45 (mt 1H of CH₂ at position 9 of the anti isomer); from 4.65 to 4.80 (mt: CH at position 3—CH at position 27 and CH at position 14 of the syn isomer); 4.85 (mt: CH at position 14 of the anti isomer); 5.40 (d, J=9 Hz: CH at position 13 of the syn isomer) 5.65 (mt: CH at position 10); from 5.70 to 5.85 (mt: CH at position 6 and CH at position 13 of the anti isomer); from 6.00 to 6.15 (mt: CONH); 6.18 and 6.22 (2 d, J=16 Hz, respectively CH at position 11 of the syn isomer and CH at position 11 of the anti isomer); 6.45 and 6.52 (2 dd, J=16 and 5 Hz: respectively CH at position 5 of the anti isomer and CH at position 5 of the syn isomer); 8.09 and 8.10 (s: respectively CH at position 20 of the syn isomer and CH at position 20 of the anti isomer).

Upon high-performance liquid chromatography starting with 16-amino-16-deoxopristinamycin II$_B$ (mixture of the (16R)/(16S) isomers=75/25), (16R)-16-amino-16-deoxopristinamycin II$_B$ is obtained in the form of a white powder melting at around 130 EC (dec.).

$^1$H NMR spectrum (400 MHz, CDCl₃, δ in ppm): 0.95 and 0.99 (2 d, J=6.5 Hz, 3H each CH₃ at position 30 and CH₃ at position 31); 1.08 (d, J=6.5 Hz, 3H: CH₃ at position 32); 1.45 (mt, 1H: 1H of CH₂ at position 15); from 1.65 to 2.00 (mt, 5H: 1H of CH₂ at position 15—CH₂ at position 25—1H of CH₂ at position 26 and CH at position 29); 1.79 (s, 3H: CH₃ at position 33); 2.12 (mt, 1H: 1H of CH₂ at position 26); from 2.70 to 2.80 (mt, 1H: CH at position 4); 2.76 and 2.98 (2 dd, respectively J=16 and 8 Hz and J=16 and 5 Hz, 1H each: CH₂ at position 17); 3.42 (mt, 1H: CH at position 16); 3.48 (mt, 1H: 1H of CH₂ at position 9); 3.93 (mt, 2H: CH₂ at position 24); 4.40 (mt, 1H: 1H of CH₂ at position 9); from 4.70 to 4.80 (mt, 3H: CH at position 3—CH at position 14 and CH at position 27); 5.42 (d, J=9 Hz, 1H: CH at position 13); 5.67 (mt, 1H: CH at position 10); 5.79 (dd, J=17 and 2.5 Hz, 1H: CH at position 6); 5.93 (mt, 1H: CONH); 6.18 (d, J=16 Hz, 1H: CH at position 11); 6.52 (dd, J=17 and 5 Hz, 1H: CH at position 5); 8.12 (s, 1H: CH at position 20).

EXAMPLE 8

16-Methylamino-16-deoxopristinamycin II$_B$

[Mixture of the (16R)/(16S) Isomers=70/30]

56 g of magnesium sulphate and 9.46 cm³ of methylamine in solution in ethanol (about 8 M) are added at about 20 EC, under an argon atmosphere, to 20 g of pristinamycin II$_B$ in solution in 280 cm³ of methanol. The reaction mixture is stirred at about 20 EC for 24 hours. The reaction mixture is then filtered on Celite, and then the Celite washed several times with methanol. 2.86 g of sodium cyanoborohydride and 9.46 cm³ of acetic acid are then added to the filtrate. After stirring the reaction mixture for 5 hours, the solution obtained is concentrated to dryness under reduced pressure (2.7 kPa) at 30 EC. The residue is dissolved in 200 cm³ of dichloromethane and then washed with a saturated aqueous sodium bicarbonate solution. The aqueous phases are decanted off and then extracted with 3H100 cm³ of dichloromethane. The organic phases are combined, dried over magnesium sulphate, filtered and then concentrated under reduced pressure (2.7 kPa) to give 17.8 g of an orange-coloured powder which is purified by flash chromatography [eluent: dichloromethane-methanol (70-30 then 60/40 by volume)]. 10.5 g of 16-methylamino-16-deoxopristinamycin II$_B$ (mixture of the (16R)/(16S) isomers=70/30 are thus isolated in the form of a yellow powder.

$^1$H NMR spectrum [syn (16R) isomer 70%, anti (16S) isomer 30%] (400 MHz, CDCl₃, δ in ppm): from 0.90 to 1.10 (mt, 9H: CH₃ at position 30—CH₃ at position 31 and CH₃ at position 32); from 1.20 to 1.40 (mt: 1H of CH₂ at position 15 of the syn isomer); from 1.65 to 2.00 (mt: 1H of CH₂ at position 15 of the syn isomer—1H of CH₂ at position 15 of the anti isomer—CH₂ at position 25— 1H of CH₂ at position 26 and CH at position 29); 1.73 and 1.77 (2 s: respectively CH₃ at position 33 of the anti isomer and CH₃ at position 33 of the syn isomer) from 2.05 to 2.15 (mt: 1H of CH₂ at position 26); 2.18 (dt, J=15 and 3 Hz, 1H of CH₂ at position 15 of the anti isomer); from 2.20 to 2.60 (broad unresolved complex: NH); 2.51 and 2.52 (2 s: respectively NCH₃ of the anti isomer and NCH₃ of the syn isomer); 2.60 (dd, J=16 and 11 Hz 1H of CH₂ at position 17 of the anti isomer); from 2.70 to 2.80 (mt: CH at position 4); 2.75 (dd, J=16 and 8 Hz: 1H of CH₂ at position 17 of the syn isomer); from 3.05 to 3.20 (mt: 1H of CH₂ at position 17 and CH at position 16 of the syn isomer); from 3.30 to 3.40 (mt: 1H of CH₂ at position 9 of the anti isomer and CH at position 16 of the anti isomer); 3.48 (mt: 1H of CH₂ at position 9 of the syn isomer); 3.83 and 3.98 (2 mts, 2 hours in total: CH₂ at position 24); 4.37 (mt: 1H of CH₂ at position 9 of the syn isomer); 4.50 (mt: 1H of CH₂ at position 9 of the anti isomer); from 4.65 to 4.80 (mt: CH at position 3—CH at position 27 and CH at position 14 of the syn isomer); 4.83 (mt: CH at position 14 of the anti isomer); 5.39 (d, J=9 Hz: CH at position 13 of the syn isomer); 5.65 (mt, 1H: CH at position 10); from 5.70 to 5.85 (mt: CH at position 6 and CH at position 13 of the anti isomer); 5.96 (mt, 1H: CONH); 6.16 and 6.23 (2 d, J=16 Hz, 1H in total: respectively CH at position 11 of the syn isomer and CH at position 11 of the anti isomer); 6.45 and 6.52 (2 dd, J=16 and 5 Hz, 1H in total: respectively CH at position 5 of the anti isomer and CH at position 5 of the syn isomer); 8.10 and 8.12 (s: respectively CH at position 20 of the syn isomer and CH at position 20 of the anti isomer).

Upon high-performance liquid chromatography starting with 16-methylamino-16-deoxopristinamycin II$_B$ (mixture of (16R)/(16S) isomers=70/30), (16R)-16-methylamino-16-deoxopristinamycin II$_B$ is obtained in the form of a yellow solid melting at around 128 EC (dec.).

$^1$H NMR spectrum (400 MHz, CDCl₃, δ in ppm): 0.96 and 1.00 (2 d, J=6.5 Hz, 3H each: CH₃ at position 30 and CH₃ at position 31); 1.08 (d, J=6.5 Hz, 3H: CH₃ at position 32); 1.33 (mt, 1H: 1H of CH₂ at position 15); from 1.60 to 2.05 (mt, 5H: 1H of CH₂ at position 15—CH₂ at position 25—1H of CH₂ at position 26 and CH at position 29); 1.75 (s, 3H: CH₃ at position 33); 2.11 (mt, 1H: 1H of CH₂ at position 26); 2.53 (s, 3H: NCH₃); 2.70 to 2.80 (mt, 1H: CH at position 4); 2.75 and 3.12 (2 dd, respectively J=16 and 8 Hz and J=16 and 4 Hz, 1H each: CH₂ at position 17); 3.10 to 3.20 (mt, 1H: CH at position 16); 3.48 (mt, 1H: 1H of CH₂ at position 9); 3.82 and 3.98 (2 mts, 1H each: CH₂ at position 24); 4.37 (mt, 1H: 1H of CH₂ at position 9); from 4.65 to 4.80 (mt, 3H: CH at position 3—CH at position 14 and CH at position 27); 5.40 (d, J=9 Hz, 1H: CH at position 13); 5.64 (mt, 1H: CH at position 10); 5.78 (dd, J=17 and 2.5 Hz, 1H: CH at position 6); 5.96 (mt, 1H: CONH); 6.16 (d, J=16 Hz, 1H: CH at position 11); 6.52 (dd, J=17 and 5 Hz, 1H: CH at position 5); 8.10 (s, 1H: CH at position 20).

EXAMPLE 9

(16R)-$^{16}$-Isopropylamino-16-deoxopristinamycin II$_B$ hydrochloride 72 g of magnesium sulphate, 8.8 g of ammonium acetate and 3.3 g of sodium cyanoborohydride are added at about 20 EC, under an argon atmosphere, to 12 g of pristinamycin II$_B$ in solution in 120 cm³ of methanol. After stirring for 20 hours, 33.5 cm³ of acetone are added and the reaction mixture is stirred for 7 hours at about 20 EC before filtering on Celite. The Celite is washed several times with dichloromethane and the pooled filtrates are concentrated to dryness under reduced pressure (2.7 kPa) at 30 EC. The residue is dissolved in 400 cm³ of dichloromethane and the solution ithus obtained is washed with 3H200 cm³ of a saturated aqueous sodium bicarbonate solution. The final organic phase is concentrated to dryness under reduced pressure (2.7 kPa) at 30 EC to give 11.3 g of an orange-coloured powder which is purified by flash chromatography [gradient elution: n-butanol-ethyl acetate-ethanol-water (10-60-15-15 then 20-50-15-15 then 30–40–15–15 by volume)] to give 2.92 g of 16-isopropylamino-16-deoxopristinamycin $II_B$ (mixture of the (16R)/(16S) isomers=75/25) in the form of a yellow powder. The two epimers are separated by centrifugal partition chromatography [eluent: ethyl acetate-hexane-methanol-water (2-1-1-1.8 by volume)] to give 0.77 g of (16R)-16-isopropylamino-16-deoxopristinamycin $II_B$ in the form of a white powder. The latter is dissolved in a mixture of 10.8 cm³ of 0.1N hydrochloric acid and 27.7 cm³ of water. The solution thus obtained is then filtered and the filtrate freeze-dried to give 0.72 g of (16R)-16-isopropylamino-16-deoxopristinamycin $II_B$ hydrochloride in the form of a white powder melting at around 135 EC (dec.).

$^1$H NMR spectrum (400 MHz, CDCl₃, δ in ppm): from 0.90 to 1.05 (mt, 6H: CH₃ at position 30 and CH₃ at position 31); 1.07 (d, J 6.5 Hz, 3H: CH₃ at position 32); 1.44 and 1.54 (2 d, J=6.5 Hz, 3H each: 2 CH₃ of isopropyl); from 1.70 to 2.25 (mt, 7H: CH₂ at position 15—CH₂ at position 25—CH₂ at position 26 and CH at position 29); 1.85 (s, 3H: CH₃ at position 33); 2.74 (mt, 1H: CH at position 4); 3.34 (mt, 2H: CH₂ at position 17); 3.45 (mt, 1H: CH of isopropyl); 3.56 (mt, 1H 1H of CH₂ at position 9); 3.67 (mt, 1H: CH at position 16); 3.82 and 3.95 (2 mts, 1H each CH₂ at position 24); 4.31 (mt, 1H: 1H of CH₂ at position 9); from 4.70 to 4.80 (mt, 2H: CH at position 3 and CH at position 27); 4.85 (mt, 1H: CH at position 14); 5.41 (d, J=9 Hz, 1H: CH at position 13); 5.75 (mt, 1H: CH at position 10); 5.83 (dd, J=16 and 2 Hz, 1H: CH at position 6); 6.22 (d, J=16 Hz, 1H: CH at position 11); 6.46 (mt, 1H: CONH); 6.54 (dd, J=16 and 5 Hz, 1H: CH at position 5); 8.10 (s: CH at position 20).

EXAMPLE 10

(16R)-16-Dimethylamino-16-deoxopristinamycin $II_B$ 50 g of magnesium sulphate and 9.5 cm³ of methylamine are added at about 20 EC, under an argon atmosphere, to 20 g of pristinamycin $II_B$ in solution in 300 cm³ of methanol. After stirring for 22 hours, the reaction mixture is cooled to –5 EC and 16.1 g of sodium triacetoxyborohydride are added. The reaction mixture is stirred for 5 hours between –5 EC and 0 EC and the temperature is allowed to return to about 20 EC over 12 hours. 11.35 g of paraformaldehyde are then added, and then after stirring for 6 hours, 16.1 g of sodium triacetoxyborohydride. The mixture is then stirred for 1 hour before adding 2.27 g of paraformaldehyde. After stirring for 16 hours, the reaction mixture is filtered onto Celite. The Celite is washed with 300 cm³ of methanol, the filtrate is concentrated to dryness under reduced pressure (2.7 kPa) to give a residue which is diluted in 500 cm³ of dichlbromethane. The organic phase is washed with 600 cm³ of a 5% aqueous sodium bicarbonate solution. The organic phase is decanted off and the aqueous phase is taken up in twice 500 cm³ of dichloromethane. The organic phases are combined, dried over magnesium sulphate, filtered and then concentrated to dryness under reduced pressure (2.7 kPa) to give 23 g of a chestnut-coloured powder which is purified by flash chromatography (eluent: dichloromethane-methanol-acetonitrile (90-5-5 by volume)). 3.4 g of (16R)-16-dimethylamino-16-deoxopristinamycin $II_B$ are thus obtained in the form of a chestnut-beige powder melting at around 122 EC (dec.)

$^1$H NMR spectrum (400 MHz, CDCl₃, δ in ppm): 0.95 and 0.98 (2 d, J=6.5 Hz, 3H each: CH₃ at position 30 and CH₃ at position 31); 1.07 (d, J=6.5 Hz, 3H: CH₃ at position 32); from 1.60 to 2.00 (mt, 6H: CH₂ at position 15—CH₂ at position 25—1H of CH₂ at position 26 and CH at position 29); 1.78 (s, 3H: CH₃ at position 33); 2.11 (mt, 1H 1H of CH₂ at position 26); 2.36 (s, 6H: N(CH₃)₂); 2.61 (dd, J=16 and 10 Hz, 1H: 1H of CH₂ at position 17); 2.72 (mt, 1H: CH at position 4); 2.98 (dd, J=16 and 4 Hz, 1H: 1H of CH₂ at position 17); 3.21 (mt, 1H: CH at position 16); 3.52 (mt, 1H: 1H of CH₂ at position 9);3.83 and 3.92 (2 mts, 1H each: CH₂ at position 24); 4.32 (mt, 1H: 1H of CH₂at position 9); 4.67 (mt, 1H: CH at position 14); 4.74 (dd, J=9 and 3 Hz, 1H: CH at position 27); 4.79 (dd, J=10 and 2 Hz, 1H: CH at position 3); 5.35 (d, J=9 Hz, 1H: CH at position 13); 5.65 (mt, 1H: CH at position 10); 5.78 (dd, J=16 and 2 Hz, 1H: CH at position 6); 6.07 (mt, 1H: CONH); 6.17 (d, J=16 Hz, 1H: CH at position 11); 6.53 (dd, J=16 and 5 Hz, 1H: CH at position 5); 8.06 (s: CH at position 20).

EXAMPLE 11

(16R)-16-(Allyl)(methyl)amino-16-deoxopristinamycin $II_B$ 20 g of magnesium sulphate and 2.3 cm³ of allylamine are added at around 20 EC, under a nitrogen atmosphere, to 7 g of pristinamycin $II_B$ in solution in 100 cm³ of methanol. After stirring for 21 hours 45 minutes, 0.5 cm³ of allylamine is added, and then after 4 hours 45 minutes, 1.67 g of sodium cyanoborohydride and then 7 cm³ of acetic acid. The reaction mixture is stirred for 4 hours 30 minutes before adding a further 100 mg of sodium cyanoborohydride. After stirring for a further 25 hours, 2.39 g of paraformaldehyde are added and the stirring is continued. The same quantity of paraformaldehyde is added three times at half-an-hour intervals and one hour after the last addition, 450 mg of sodium cyanoborohydride, 3.5 cm³ of acetic acid and again 2.39 g of paraformaldehyde are added. After stirring for 19 hours 30 minutes, the mixture is filtered on Celite and then rinsed with methanol. The filtrate is concentrated to dryness under reduced pressure (2.7 kPa) at 30 EC and the residue obtained is then taken up in 300 cm³ of methylene chloride and 600 cm³ of a 5% sodium bicarbonate solution. The aqueous phase is decanted off and then extracted with 200 cm³ of methylene chloride. The organic phases are pooled, washed with 300 cm³ of distilled water, dried over magnesium sulphate, filtered and then concentrated to dryness under reduced pressure (2.7 kPa) to give a solid which is dried under reduced pressure (90 Pa) at 20 EC and then purified by flash chromatography [eluent: dichloromethane-methanol (95-5 by volume)]. 1.25 g of (16R)-16-(allyl)(methyl)amino-16-deoxopristinamycin $II_B$ are obtained in the form of an off-white solid melting at around 124 EC (dec.).

$^1$H NMR spectrum (400 MHz, CDCl₃, δ in ppm): 0.95 and 0.99 (2 d, J=6.5 Hz, 3H each: CH₃ at position 30 and CH₃ at position 31); 1.08 (d, J=6.5 Hz, 3H: CH₃ at position 32); from 1.65 to 2.00 (mt, 6H: CH₂ at position 15—CH₂ at position 25—1H of CH₂ at position 26 and CH at position 29); 1.78 (s, 3H: CH₂ at position 33); 2.12 (mt, 1H: 1H of CH₂ at position 26); 2.32 (s, 3H: NCH₃); 2.64 and 2.98 (2 dd, respectively J=16 and 10 Hz and J=16 and 4 Hz, 1H each: CH₂ at position 17); 2.73 (mt, 1H: CH at position 4); 3.05 and 3.28 (2 dd, respectively J=14 and 7 Hz and J=14 and 6 Hz, 1H each: CH₂ of N(allyl)); 3.35 (mt, 1H: CH at position 16); 3.52 (mt, 1H: 1H of CH₂ at position 9); 3.84 and 3.93 (2 mts, 1H each: $CH_2$ at position 24); 4.34 (mt, 1H: 1H of $CH_2$ at position 9); 4.67 (mt, 1H CH at position 14); 4.75 (dd, J=9 and 2.5 Hz, 1H: CH at position 27); 4.80 (dd, J=8 and 1.5 Hz, 1H: CH at position 3); 5.19 and 5.23 (respectively d, J=10 Hz and dd, J=18 and 1.5 Hz, 1H each: =$CH_2$ of allyl); 5.36 (d, J=9 Hz, 1H: CH at position 13); 5.67 (mt, 1H: CH at position 10); 5.80 (dd, J=17 and 2.5 Hz, 1H: CH at position 6); from 5.80 to 5.95 (mt, 1H: CH=of allyl); 6.02 (mt, 1H CONH); 6.18 (d, J=16 Hz, 1H: CH at position 11); 6.53 (dd, J=17 and 5 Hz, 1H: CH at position 5); 8.07 (s, 1H: CH at position 20).

EXAMPLE 12

16-Propyn-2-ylamino-16-deoxopristinamycin $II_A$
[Mixture of the (16R)/(16S) isomers=65/35]

0.130 $cm^3$ of propargylamine and then 0.053 $cm^3$ of acetic acid are added at a temperature close to 20 EC, under an argon atmosphere, to 0.5 g of pristinamycin $II_A$ in solution in 70 $cm^3$ of anhydrous acetonitrile. The mixture is stirred for 18 hours at a temperature close to 20 EC and then a further 0.13 $cm^3$ of propargylamine is added. The mixture is stirred for 4 hours at a temperature of 20 EC and is then concentrated under reduced pressure (2.7 kPa) at a temperature close to 30 EC until an insoluble material appears. 0.072 g of sodium cyanoborohydride and then 1.2 $cm^3$ of concentrated acetic acid are then added at a temperature close to 20 EC, under an argon atmosphere. The mixture is stirred for 1 hour 30 minutes at a temperature close to 20 EC. The reaction mixture is concentrated to dryness under reduced pressure (2.7 kPa). The residue obtained is then taken up in dichloromethane and the organic phase washed twice with a saturated aqueous sodium bicarbonate solution. The aqueous phases are combined and extracted with dichloromethane. The organic phases are combined, dried over magnesium sulphate, filtered on sintered glass and then concentrated to dryness under reduced pressure (2.7 kPa). The residue obtained is purified by preparative plate chromatography (Merck silica gel 60 $F_{254}$; thickness=2 mm, 20H20 cm), eluting with a dichloromethane-methanol-acetonitrile (90-5-5 by volume) mixture to give 0.205 g of 16-propyn-2-ylamino-16-deoxopristinamycin $II_A$ (mixture of the (16R)/(16s) isomers=65/35) in the form of a beige powder.

$^1$H NMR spectrum [syn (16R) isomer 65% and anti (16S) isomer 35%] (400 MHz, $CDCl_3$, δ in ppm): from 0.90 to 1.05 (mt, 6H: $CH_3$ at position 30 and $CH_3$ at position 31 ; from 1.05 to 1.20 (mt, 3H: $CH_3$ at position 32); from 1.50 to 2.10 (mt: $CH_2$ at position 15 and CH at position 29); 1.64 and 1.74 (2 s: respectively $CH_3$ at position 33 of the anti isomer and $CH_3$ at position 33 of the syn isomer); 2.27 and 2.32 (2 t, J=2.5 Hz: respectively CH of 2-propynyl of the syn isomer and CH of 2-propynyl of the anti isomer); from 2.55 to 2.95 (mt: $CH_2$ at position 25—1H of $CH_2$ at position 17—CH at position 16 of the syn isomer and CH at position 4); 3.00 (dd, J=14 and 2.5 Hz: 1H of $CH_2$ at position 17 of the syn isomer); 3.22 (dd, J=14 and 2.5 Hz: 1H of $CH_2$ at position 17 of the anti isomer); 3.36 (mt: 1H of $CH_2$ at position 9 of the anti isomer); from 3.45 to 3.60 (mt: $NCH_2$ of 2-propynyl and CH at position 16 of the anti isomer); 3.82 (broad d, J=18 Hz: 1H of $CH_2$ at position 9 of the syn isomer); from 4.10 to 4.60 (mt: $CH_2$ at position 24—1H of $CH_2$ at position 9 and CH at position 14 of the syn isomer); from 4.75 to 4.85 (mt: CH at position 14 of the anti isomer and CH at position 13 of the syn isomer); from 4.90 to 5.00 (mt, 1H: CH at position 3); from 5.45 to 5.60 (mt: CH at position 10 of the anti isomer); 5.50 (d, J=8 Hz: CH at position 13 of the anti isomer); 5.64 (mt: CH at position 10 of the syn isomer); from 5.80 to 6.10 (mt: CH at position 6—CH at position 11 and CH at position 26 of the anti isomer); 6.13 (t, J=3 Hz: CH at position 26 of the syn isomer); 6.53 (dd, J 16 and 6 Hz: CH at position 5 of the anti isomer); from 6.55 to 6.70 (mt: CONH of the anti isomer); 6.61 (dd, J=16 and 7 Hz; CH at position 5 of the syn isomer); 7.48 (mt: CONH of the syn isomer); 7.87 and 8.08 (2 s: respectively CH at position 20 of the syn isomer and CH at position 20 of the anti isomer).

EXAMPLE 13

16-Allylamino-16-deoxopristinamycin $II_A$
[Mixture of the (16R)/(16S) Isomers=65/35]

0.054 $cm^3$ of acetic acid is added to a suspension of 0.5 g of pristinamycin $II_A$ in 15 $cm^3$ of acetonitrile and 0.143 $cm^3$ of allylamine, kept at a temperature close to 20 EC. After one hour at a temperature close to 20 EC, 0.072 g of sodium cyanoborohydride and then 1 $cm^3$ of acetic acid are added successively. After one hour at a temperature close to 20 EC, 7 $cm^3$ of water and 15 $cm^3$ of dichloromethane are added to the reaction mixture. The organic phase is decanted off and then washed with twice 10 $cm^3$ of a saturated sodium bicarbonate solution. The aqueous phases are extracted with 10 $cm^3$ of dichloromethane. The pooled organic phases are dried over magnesium sulphate, filtered and concentrated under reduced pressure (about 2.7 kPa) at a temperature close to 40 EC. A bright yellow foam is thus obtained which is purified by preparative thin-layer chromatography: 6 Merck preparative plates, Kieselgel 60 $F_{254}$, 20H20 cm, thickness 2 mm, deposition in solution in dichloromethane, eluting with a dichloromethane-methanol-acetonitrile (80-10-10 by volume) mixture to give 0.179 g of 16-allylamino-16-deoxopristinamycin $II_A$ (mixture of the (16R)/(16S) isomers=65/35) in the form of a cream-coloured foam.

$^1$H NMR spectrum [mixture of the (16R)/(16S) isomers=65/35] (400 MHz, $CDCl_3$, δ in ppm): from 0.95 to 1.05 (mt, 6H: $CH_3$ at position 30 and $CH_3$ at position 31); from 1.10 to 1.20 (mt, 3H: $CH_3$ at position 32); 1.64 and 1.71 (2 s, 3H in total: respectively $CH_3$ at position 33 of the anti isomer and $CH_3$ at position 33 of the syn isomer); from 1.70 to 2.10 (mt, 3H: $CH_2$ in position 15 and CH in position 29); from 2.60 to 2.90 (mt: $CH_2$ at position 25—1H from $CH_2$ at position 17—CH at position 16 of the syn isomer and CH at position 4); 3.06 (broad d, J=14 Hz: 1H of $CH_2$ at position 17 of the syn isomer); 3.22 (broad d, J 15 Hz: 1H of $CH_2$ at position 17 of the anti isomer); from 3.30 to 3.55 (mt: 1H of $CH_2$ at position 9 of the anti isomer—$NCH_2$ of allyl and CH at position 16 of the anti isomer); 3.85 (broad d, J=18 Hz: 1H of $CH_2$ at position 9 of the syn isomer); from 4.10 to 4.60 (mt: $CH_2$ at position 24—1H of $CH_2$ at position 9 and CH at position 14 of the syn isomer); 4.80 (mt: CH at position 14 of the anti isomer); 4.87 (broad d, J=8 Hz: CH at position 13 of the syn isomer); from 4.90 to 5.00 (mt, 1H: CH at position 3); from 5.15 to 5.30 (mt: =$CH_2$ of allyl); from 5.45 to 5.60 (mt: CH at position 10 of the anti isomer); 5.55 (d, J=9 Hz: CH at position 13 of the anti isomer); 5.63 (mt: CH at position 10 of the syn isomer); from 5.85 to 6.10 (mt: CH at position 6—CH at position 11—CH at position 26 of the anti isomer and =CH of allyl); 6.14 (broad s: CH at position 26 of the syn isomer); from 6.45 to 6.60 (mt: CH at position 5 of the anti isomer and CONH of the anti isomer); 6.62 (dd, J=16 and 7 Hz: CH at position 5 of the syn isomer); 7.39 (mt: CONH of the syn isomer); 7.88 and 8.07 (2 s: respectively CH at position 20 of the syn isomer and CH at position 20 of the anti isomer).

EXAMPLE 14

(16R)-16-Dimethylamino-16-deoxopristinamycin II$_A$ 6.9 cm$^3$ of methylamine (8 M in ethanol) and then 1.43 cm$^3$ of acetic acid are added at a temperature close to 20 EC, under an argon atmosphere, to 28.5 g of pristinamycin II$_A$ in solution in 780 cm$^3$ of anhydrous acetonitrile. The mixture is stirred for 48 hours at a temperature close to 20 EC and then 3.8 g of sodium cyanoborohydride and 12 cm$^3$ of acetic acid are added under an argon atmosphere. The mixture is stirred for 3 hours at a temperature close to 20 EC before a further addition of 11 cm$^3$ of acetic acid. The reaction mixture is again stirred for 7.5 hours at a temperature close to 20 EC. 6 g of paraformaldehyde are then added and the mixture is kept stirred for 17 hours at a temperature close to 20 EC. The white suspension obtained is filtered and the filtrate is concentrated under reduced pressure (2.7 kPa) at a temperature close to 30 EC. The residual thick oil is then taken up in 800 cm$^3$ of ethyl acetate and in 300 cm$^3$ of water. After stirring for about 15 minutes, the pH of the solution obtained is adjusted first to 9 by addition of concentrated sodium hydroxide, and then to 11 by addition of 150 cm$^3$ of 1 N. sodium hydroxide. The mixture obtained is stirred for about one hour before a further addition of 50 cm$^3$ of 1 N sodium hydroxide and stirring for a further one hour approximately. The resulting mixture is separated after settling out and the organic phase washed with twice with 100 cm$^3$ of water and then extracted three times with 1 N HCl (1000 cm$^3$, 100 cm$^3$ and 50 cm$^3$ successively). The pooled acidic aqueous phases are extraced with 200 cm$^3$ of ether and then alkalinized to pH 10–11 by addition of 23 cm$^3$ of concentrated sodium hydroxide. The aqueous phase obtained is extracted with twice 300 cm$^3$ of dichloromethane and the organic phases are combined, washed with 100 cm$^3$ of water, dried over magnesium sulphate, filtered on sintered glass and then concentrated to dryness under reduced pressure (2.7 kPa) at a temperature close to 30 EC to give a white solid. The latter is stirred in 200 cm$^3$ of ether and then filtered and dried to constant weight (90 Pa, at about 20 EC), to give 20 g of a white powder. The latter is purified by flash chromatography (eluent: dichloromethane-methanol-acetonitrile (92-4-4 then 84-8-8 by volume))] to give 5.2 g of (16R)-16-dimethylamino-16-deoxopristinamycin II$_A$ in the form of a white solid. 4.5 g of this solid are recrystallized from an acetonitrile-water (18 cm$^{3-9}$ cm$^3$) mixture to give, after draining and drying under reduced pressure (90 Pa, at about 20 EC), 3.46 g of a white powder melting at around 212 EC.

$^1$H NMR spectrum (400 MHz, CDCl$_3$, δ in ppm): from 0.90 to 1.05 (mt, 6H: CH$_2$ at position 30 and CH$_3$ at position. 31); 1.13 (d, J=6.5 Hz, 3H: CH$_3$ at position 32); 1.63 (mt, 1H: 1H of CH$_2$ at position 15); 1.73 (s, 3H: CH$_3$ at position 33); from 1.95 to 2.10 (mt, 2H: 1H of CH$_2$ at position 15 and CH at position 29); 2.36 (s, 6H: N(CH$_3$)$_2$); from 2.50 to 2.65 (mt, 2H 1H of CH$_2$ at position 17 and CH at position 16); from 2.65 to 2.75 (mt, 2H: CH at position 4 and 1H of CH$_2$ at position 25); from 2.80 to 2.95 (mt, 1H: 1H of CH$_2$ at position 25); 2.97 (d, J=11 Hz, 1H: 1H of CH$_2$ at position 17); 3.79 (broad d, J=18 Hz, 1H: 1H of CH$_2$ at position 9); 4.21 (mt, 1H: 1H of CH$_2$ at position 24); from 4.30 to 4.50 (mt, 3H: 1H of CH$_2$ at position 9—1H of CH$_2$ at position 24 and CH at position 14); 4.79 (d, J=9 Hz, 1H: CH at position 13); 4.97 (dd, J=10 and 1.5 Hz, 1H: CH at position 3); 5.64 (mt, 1H: CH at position 10); 5.90 (broad d, J=16 Hz, 1H: CH at position 11); 6.04 (d, J=16 Hz, 1H: CH at position 6); 6.13 (t, J=3 Hz, 1H: CH at position 26); 6.62 (dd, J=17 and 5 Hz, 1H: CH at position 5); 7.51 (mt, 1H CONH); 7.87 (s: CH at position 20).

EXAMPLE 15

(16R)-16-Methylamino-16-deoxopristinamycin II$_A$

By carrying out the procedure as described in Examples 12 and 13, starting with pristinamycin II$_A$, (16R)-16-methylamino-16-deoxopristinamycin II$_A$ is obtained in the form of a cream-coloured foam melting at around 130 EC (dec.).

$^1$H NMR spectrum (400 MHz, CDCl$_3$, δ in ppm): from 0.90 to 1.05 (mt, 6H; CH$_3$ at position 30 and CH$_3$ at position 31); 1.12 (d, J=6.5 Hz, 3H: CH$_3$ at position 32); 1.72 (s, 3H: CH$_3$ at position 33); from 1.80 to 2.10 (mt, 3H: CH$_2$ at position 15 and CH at position 29); 2.58 (s, 3H: NCH$_3$); from 2.60 to 2.90 (mt, 4H: CH at position 4—1H of CH$_2$ at position 17 and CH$_2$ at position 25); 3.12 (dd, J=14 and 1.5 Hz, 1H 1H of CH$_2$ at position 17); from 3.35 to 3.45 (mt, 1H: CH at position 16); 3.86 (broad d, J=18 Hz, 1H: 1H of CH$_2$ at position 9); from 4.18 to 4.40 (mt, 3H: 1H of CH$_2$ at position 9 and CH$_2$ at position 24); 4.55 (mt, 1H: CH at position 14); 4.89 (d, J=9 Hz, 1H: CH at position 13); 4.93 (dd, J=10 and 1.5 Hz, 1H: CH at position 3); 5.62 (mt, 1H: CH at position 10); 5.90 (d, J=16 Hz, 1H: CH at position 11); 6.01 (d, J=16 Hz, 1H: CH at position 6); 6.14 (t, J=3 Hz, 1H: CH at position 26); 6.61 (dd, J=17 and 5 Hz, 1H: CH at position 5); 7.38 (mt, 1H: CONH); 7.90 (s, 1H: CH at position 20).

EXAMPLE 16

16-Benzylamino-16-deoxopristinamycin II$_A$

[Mixture of the (16R)/(16S) Isomers=50/50]

By carrying out the procedure as described in Examples 12 and 13, starting with pristinamycin II$_A$, 16-benzylamino-16-deoxopristinamycin II$_A$ [mixture of the (16R)/(16S) isomers=50/50) is obtained in the form of a white powder.

$^1$H NMR spectrum (syn (16R) isomer 50% and anti (16S) isomer 50%] (400 MHz, CDCl$_3$, δ in ppm): from 0.95 to 1.05 (mt, 6H: CH$_3$ at position 30 and CH$_3$ at position 31); from 1.05 to 1.20 (mt, 3H: CH$_3$ at position 32); 1.45 and 1.63 (2 s: respectively CH$_3$ at position 33 of the anti isomer and CH$_3$ at position 33 of the syn isomer); from 1.50 to 2.15 (mt, the 3H corresponding to: CH$_2$ at position 15 and CH at position 29); from 2.60 to 2.95 (mt: CH$_2$ at position 25—1H of CH$_2$ at position 17 of the anti isomer—CH$_2$ at position 17 of the syn isomer and CH at position 4); 3.12 (mt: CH at position 16 of the syn isomer); 3.29 (broad d, J=15 Hz: 1H of CH$_2$ at position 17 of the anti isomer); 3.35 (mt: 1H of CH$_2$ at position 9 of the anti isomer); 3.47 (mt: CH at position 16 of the anti isomer); from 3.80 to 4.10 (mt: 1H of CH$_2$ at position 9 of the syn isomer and NCH$_2$ of benzyl); from 4.10 to 4.45 (mt: CH$_2$ at position 24—H of CH$_2$ at position 9 of the syn isomer and CH at position 14 of the syn isomer); 4.54 (mt: 1H of CH$_2$ at position 9 of the anti isomer); from 4.75 to 4.85 (mt: CH at position 14 of the anti isomer and CH at position 13 of the syn isomer); from 4.90 to 5.00 (mt, 1H: CH at position 3); 5.40 (d, J=8 Hz: CH at position 13 of the anti isomer); from 5.45 to 5.65 (mt, 1H: CH at position 10); from 5.80 to 6.05 (mt, 2H at position 6 and CH at position 11); 6.08 and 6.14 (2 t, J=3 Hz, 1H in total: respectively CH at position 26 of the anti isomer and CH at position 26 of the syn isomer); from 6.45 to 6.55 (mt: CONH of the anti isomer); 6.54 (dd, J=16 and 6 Hz: CH at position 5 of the anti isomer); 6.61 (dd, J=16 and 7 Hz: CH at position 5 of the syn isomer); from 7.25 to 7.45 (mt: 5H of phenyl and CONH of the syn isomer); 7.86 and 8.09 (2 s: respectively CH at position 20 of the syn isomer and CH at position 20 of the anti isomer).

EXAMPLE 17

(16R)-16-Methoxyamino-16-deoxopristinamycin $II_B$ 10 g of pristinamycin $II_B$ O-methyloxime (70/30 mixture of the Z and E isomers) in solution in 300 cm³ of methanol and 100 cm³ of acetic acid are placed in a round-bottomed flask kept under a nitrogen atmosphere. The mixture is cooled to −70 °C before adding 10.3 g of sodium cyanoborohydride. The temperature is allowed risen slowly to about 20 °C and the reaction mixture is left unstirred for 48 hours. An argon stream is passed for one hour through the solution kept under an aspirating fume cupboard and then the solvents are evaporated off under reduced pressure (2.7 kPa) at 20 °C and the residue is taken up in 200 cm³ of methylene chloride and 100 cm³ of distilled water. The aqueous phase is alkalinized to pH 8 by addition of 30 cm³ of concentrated NaOH and the mixture is stirred for 30 minutes before being transferred into a separating funnel. The organic phase is decanted off and then washed with twice 100 cm³ of distilled water. The organic phase is decanted off, dried over magnesium sulphate, filtered and then concentrated under reduced pressure (2.7 kPa) at 20 °C to give a colourless oil which is stirred in diethyl ether; the precipitate obtained is filtered. 9.1 g of a white powder are thus obtained, which powder is purified by flash chromatography (eluent: $CH_2Cl_2$—MeOH 97-3 by volume). 1.88 g of (16R)-16-methoxyamino-16-deoxopristinamycin $II_B$ are isolated in the form of a white powder melting at 195 °C.

¹H NMR spectrum (600 MHz, $CDCl_3$, δ in ppm): 0.95 and 1.00 (2 d, J=6.5 Hz, 3H each: $CH_3$ at position 30 and $CH_3$ at position 31); 1.07 (d, J=6.5 Hz, 3H: $CH_3$ at position 32); from 1.60 to 2.00 (mt, 6H: $CH_2$ at position 15—$CH_2$ at position 25—1H of $CH_2$ at position 26 and CH at position 29); 1.80 (s, 3H: $CH_3$ at position 33); 2.15 (mt, 1H: 1H of $CH_2$ at position 26); from 2.70 to 2.80 (mt, 1H: CH at position 4); 2.76 and 3.24 (2 dd, respectively J=16 and 8 Hz and J=16 and 4 Hz, 1H each: $CH_2$ at position 17); from 3.45 to 3.55 (mt, 2H: CH at position 16 and 1H of $CH_2$ at position 9); 3.60 (s, 3H; $OCH_3$); 3.92 (mt, 2H: $CH_2$ at position 24); 4.43 (mt, 1H: 1H of $CH_2$ at position 9); from 4.70 to 4.80 (mt, 3H: CH at position 3—CH at position 14 and CH at position 27); 5.34 (d, J=9 Hz, 1H: CH at position 13); 5.70 (mt, 1H: CH at position 10); 5.80 (dd, J=16 and 2 Hz, 1H: CH at position 6); 6.14 (mt, 1H: CONH); 6.18 (d, J=16 Hz, 1H: CH at position 11); 6.51 (dd, J=16 and 5 Hz, 1H: CH at position 5); 8.09 (s, 1H: CH at position 20).

Pristinamycin $II_B$ O-methyloxime (70/30 mixture of the Z and E isomers) may be prepared in the following manner:

20 g of pristinamycin $II_B$ in solution in 800 cm³ of anhydrous pyridine are placed in a three-necked flask and 4.2 g of methoxyamine hydrochloride are added. After stirring for 21 hours, the pyridine is evaporated off under reduced pressure (2.7 kPa) at 40 °C and then the residue obtained is taken up in 500 cm³ of methylene chloride and 1 litre of distilled water. The organic phase is decanted off, washed with twice 1 litre of distilled water, dried over sodium sulphate, filtered and then concentrated to dryness under reduced pressure (2.7 kPa) at 40 °C to give a residue which is stirred in 300 cm³ of diethyl ether. The precipitate is filtered, dried under reduced pressure (90 Pa) and then purified by flash chromatography (eluent: $CH_2Cl_2$—MeOH 95-5 by volume). 16.9 g of pristinamycin $II_B$ O-methyloxime (70/30 mixture of the Z and E isomers) are thus obtained in the form of a white solid melting at around 198–199 °C (dec.) and which is used as it is in subsequent operations.

¹H NMR spectrum (300 MHz, $CDCl_3$, δ in ppm): from 0.90 to 1.10 (mt, 9H: $CH_3$ at position 30—$CH_3$ at position 31 and $CH_3$ at position 32); 1.73 and 1.74 (2 s, 3H in total: respectively $CH_3$ at position 33 of the E isomer and $CH_3$ at position 33 of the Z isomer); from 1.75 to 2.35 (mt: $CH_2$ at position 25—$CH_2$ at position 26—CH at position 29 and 1H of $CH_2$ at position 15 of the E isomers); 2.51 and 2.65 (2 dd, respectively J=17 and 6 Hz and J=17 and 5 Hz: $CH_2$ at position 15 of the Z isomer); from 2.65 to 2.80 (mt, 1H: CH at position 4); 3.00 (dd, J=13 and 6 Hz: 1H of $CH_2$ at position 15 of the E isomer); 3.22 (d, J=6 Hz: OH of the Z isomer); from 3.30 to 3.45 (mt, 1H: 1H of $CH_2$ at position 9); 3.58 and 3.68 (2 d, J=15 Hz: $CH_2$ at position 17 of the E isomer); from 3.65 to 3.80 (mt, 1H: 1H of $CH_2$ at position 24); 3.62 and 4.04 (2 d, J=16.5 Hz: $CH_2$ at position 17 of the Z isomer); 3.92 and 3.94 (2 s, 3H in total: respectively $OCH_3$ of the Z isomer and $OCH_3$ of the E isomer); from 3.95 to 4.20 (mt, 1H: 1H of $CH_2$ at position 24); 4.35 to 4.55 (mt, 1H: 1H of $CH_2$ at position 9); from 4.60 to 4.80 (mt, 2H: CH at position 3 and CH at position 27); from 4.80 to 4.90 (mt: CH at position 13 of the E isomer and CH at position 14 of the Z isomer); 5.06 (mt: CH at position 14 of the E isomer); 5.57 (d, J=9 Hz: CH at position 13 of the Z isomer); from 5.60 to 5.90 (mt, 2H: CH at position 10 and CH at position 6); 6.05 and 6.14 (2 d, J=16 Hz, 1H in total respectively CH at position 11 of the E isomer and CH at position 11 of the Z isomer); 6.28 (mt: CONH of the Z isomer); 6.47 (d, J=16 and 5 Hz, 1H: CH at position 5); 7.47 (mt: CONH of the E isomer); 7.77 (s: CH at position 20 of the E isomer); 8.08 (s: CH at position 20 of the Z isomer).

EXAMPLE 18

(16R)-16-Ethoxyamino-16-deoxopristinamycin $II_B$

By carrying out the procedure as in Example 17, but starting with 1.53 g of pristinamycin $II_B$ O-ethyloxime (50/50 mixture of the E and Z isomers) in solution in 45 cm³ of methanol, 15 cm³ of acetic acid and 1.67 g of sodium cyanoborohydride and after 67 hours of reaction, 1.4 g of a white solid are obtained, which solid is purified by flash chromatography (eluent $CH_2Cl_2$—MeOH 97/3 by volume) to give 360 mg of (16R)-16-ethoxyamino-16-deoxopristinamycin $II_B$ in the form of a white solid melting at 205 °C.

¹H NMR spectrum (400 MHz, $CDCl_3$, δ in ppm): 0.96 and 1.00 (2 d, J=6.5 Hz, 3H each: $CH_3$ at position 30 and $CH_3$ at position 31); 1.08 (d, J=6.5 Hz, 3H: $CH_3$ at position 32); 1.19 (t, J=7 Hz, 3H: $CH_3$ of ethyl); from 1.60 to 2.00 (mt, 6 H: $CH_2$ at position 15—$CH_2$ at position 25—1H of $CH_2$ at position 26 and CH at position 29); 1.80 (s, 3H: $CH_3$ at position 33); 2.14 (mt, 1H: 1H of $CH_2$ at position 26); from 2.70 to 2.80 (mt, 1H: CH at position 4); 2.76 and 3.26 (2 dd, respectively, J=16 and 8 Hz and J=16 and 4 Hz, 1H each: $CH_2$ at position 17); from 3.45 to 3.55 (mt, 2H CH at position 16 and 1H of $CH_2$ at position 9); 3.79 (q, J=7 Hz, 2H: $CH_2$ of ethyl); 3.93 (mt, 2H: $CH_2$ at position 24); 4.43 (mt, 1H: 1H of $CH_2$ at position 9); from 4.70 to 4.80 (mt, 3H: CH at position 3—CH at position 14 and CH at position 27); 5.34 (d, J=9 Hz, 1H: CH at position 13); 5.70 (mt, 1H: CH at position 10); 5.80 (dd, J=16 and 2 Hz, 1H: CH at position 6); 6.13 (mt, 1H: CONH); 6.17 (d, J=16 Hz, 1H: CH at position 11); 6.51 (dd, J=16 and 5 Hz, 1H: CH at position 5); 8.08 (s, 1H: CH at position 20).

Pristinamycin $II_B$ O-ethyloxime (70/30 mixture of the Z and E isomers) may be prepared by carrying out the procedure as in Example 17, but starting with 12 g of pristinamycin $II_B$, 2.44 g of O-ethyl hydroxylamine hydrochloride in 400 cm³ of pyridine. After extraction and stirring in diethyl ether, 11.28 g of pristinamycin $II_B$ O-ethyloxime (70/30 mixture of the Z and E isomers) are obtained in the form of a light yellow solid melting at around 114 °C (dec.) and which is used as it is for subsequent operations.

$^1$H NMR spectrum of the 70/30 mixture of the two Z/E isomers (400 MHz, CDCl$_3$, δ in ppm): from 0.90 to 1.10 (mt, 9H: CH$_3$ at position 30—CH$_3$ at position 31 and CH$_3$ at position 32); from 1.25 to 1.35 (mt, 3H: CH$_3$ of ethyl); 1.70 and 1.75 (2 s, 3H in total: respectively CH$_3$ at position 33 of the E isomer and CH$_3$ at position 33 of the Z isomer); from 1.75 to 2.35 (mt: CH$_2$ at position.25—CH$_2$ at position 26—CH at position 29 and 1H of CH$_2$ at position 15 of the E isomer); 2.52 and 2.68 (2 dd, respectively J=16.5 and 6 Hz and J=16.5 and 5 Hz: CH$_2$ at position 15 of the Z isomer); from 2.70 to 2.80 (mt, 1H: CH at position 4); 3.02 (dd, J=13 and 5 Hz: 1H of CH$_2$ at position 15 of the E isomer); 3.25 (d, J=6 Hz: OH of the Z isomer); from 3.30 to 3.45 (mt, 1H: 1H of CH$_2$ at position 9); 3.61 and 3.72 (2 d, J=15 Hz: CH$_2$ at position 17 of the E isomer); from 3.70 to 3.80 (mt, 1H: 1H of CH$_2$ at position 24); 3.63 and 4.07 (2 d, J=16 Hz: CH$_2$ at position 17 of the Z isomer); from 4.00 to 4.25 (mt, 3H: 1H of CH$_2$ at position 24 and OCH$_2$); from 4.40 to 4.55 (mt, 1H: 1H of CH$_2$ at position 9); from 4.65 to 4.90 (mt: CH at position 27—CH at position 3 and CH at position 14 of the Z isomer); 4.91 (d, J=9 Hz: CH at position 13 of the E isomer); 5.08 (mt: CH at position 14 of the E isomer); 5.59 (d, J=9 Hz: CH at position 13 of the Z isomer); from 5.65 to 5.80 (mt, 1H: CH at position 10); 5.79 and 5.85 (2 dd, respectively J=17 and 2 Hz and J=17 and 1.5 Hz, 1H in total: CH at position 6 of the Z isomer and CH at position 6 of the E isomer); 6.06 and 6.15 (2 d, J=16 Hz, 1H in total: respectively CH at position 11 of the E isomer and CH at position 11 of the Z isomer); 6.24 (mt: CONH of the Z isomer); from 6.40 to 6.55 (mt, 1H: CH at position 5); 7.43 (mt: CONH of the E isomer); 7.79 (s: CH at position 20 of the E isomer); 8.09 (s: CH at position 20 of the Z isomer).

EXAMPLE 19

(16R)-16-Allyloxyamino-16-deoxopristinamycin II$_B$

By carrying out the procedure as in Example 17, but starting with 1.46 g of pristinamycin II$_B$ O-allyloxime (65/35 mixture of the Z/E isomers) in solution in 42 cm$^3$ of methanol, 14 cm$^3$ of acetic-acid and 1.57 g of sodium cyanoborohydride and after 96 hours of reaction, 1.3 g of a white solid are isolated, which solid is purified by flash chromatography (eluent (CH$_2$Cl$_2$—MeOH 97/3 by volume) to give 0.31 g of (16R)-16-allyloxyamino-16-deoxopristinamycin II$_B$ in the form of a white solid melting at 130 EC.

$^1$H NMR spectrum (400 MHz, CDCl$_3$, δ in ppm) 0.95 and 1.00 (2 d, J=6.5 Hz, 3H each: CH$_3$ at position 30 and CH$_3$ at position 31); 1.07 (d, J=6.5 Hz, 3H: CH$_3$ at position 32); from 1.60 to 2.05 (mt, 6H: CH$_2$ at position 15—CH$_2$ at position 25—1H of CH$_2$ at position 26 and CH at position 29); 1.80 (s, 3H: CH$_3$ at position 33); 2.14 (mt, 1H: 1H of CH$_2$ at position 26); 2.24 (broad s, 1H: OH); from 2.70 to 2.85 (mt, 1H: CH at position 4); 2.77 and 3.27 (2 dd, respectively J=16 and 8 Hz and J=16 and 4 Hz, 1H each: CH$_2$ at position 17); from 3.45 to 3.55 (mt, 2H: CH at position 16 and 1H of CH$_2$ at position 9); 3.92 (mt, 2H: CH$_2$ at position 24); 4.25 (mt, 2H: CH$_2$O); 4.43 (mt, 1H: 1H of CH$_2$ at position 9); from 4.70 to 4.80 (mt, 3H: CH at position 3—CH at position 14 and CH at position 27); 5.23 and 5.30 (2 dd, respectively J=10 and 1.5 Hz and J=18 and 1.5 Hz, 1H each: =CH$_2$ of allyl); 5.34 (d, J=9 Hz, 1H: CH at position 13); 5.60 (unresolved complex, 1H: NH); 5.70 (mt, 1H: CH at position 10); 5.80 (dd, J=16 and 2 Hz, 1H: CH at position 6); 5.95 (mt, 1H: CH of allyl); 6.12 (mt, 1H CONH); 6.18 (d, J=16 Hz, 1H: CH at position 11); 6.51 (dd, J=16 and 5 Hz, 1H: CH at position 5); 8.09 (s, 1H: CH at position 20).

Pristinamycin II$_B$ O-allyloxime (65/55 mixture of the Z and E isomers) may be prepared by carrying out the procedure as in Example 17, but starting with 5 g of pristinamycin II$_B$, 1.14 g of O-allylhydroxylamine hydrochloride in 200 cm$^3$ of pyridine. After extraction and stirring in diethyl ether, 4.2 g of pristinamycin II$_B$ O-allyloxime (65/55 mixture of the Z and E isomers) are obtained in the form of an ochre-coloured solid melting at 102–104 EC and which solid is used as it is for subsequent operations.

$^1$H NMR spectrum (300 MHz, CDCl$_3$, δ in ppm) from 0.90 to 1.10 (mt, 9H: CH$_3$ at position 30—CH$_3$ at position 31 and CH$_3$ at position 32); 1.73 and 1.74 (2 s, 3H in total: respectively CH$_3$ at position 33 of the E isomer and CH$_3$ at position 33 of the Z isomer); from 1.75 to 2.35 (mt: CH$_2$ at position 25—CH$_2$ at position 26—CH at position 29 and 1H of CH$_2$ at position 15 of the E isomer); 2.51 and 2.65 (2 dd, respectively J=17 and 6 Hz and J=17 and 5 Hz: CH$_2$ at position 15 of the Z isomer); from 2.65 to 2.80 (mt, 1H: CH at position 4); 3.00 (dd, J=13 and 6 Hz: 1H of CH$_2$ at position 15 of the E isomer); 3.22 (d, J=6 Hz: OH of the Z isomer); from 3.30 to 3.45 (mt, 1H: 1H of CH$_2$ at position 9); 3.58 and 3.68 (2 d, J=15 Hz: CH$_2$ at position 17 of the E isomer); from 3.65 to 3.80 (mt, 1H: 1H of CH$_2$ at position 24); 3.62 and 4.04 (2 d, J=16.5 Hz: CH$_2$ at position 17 of the Z isomer); 3.92 and 3.94 (2 s, 3H in total: respectively OCH$_3$ of the Z isomer and OCH$_3$ of the E isomer); from 3.95 to 4.20 (mt, 1H: 1H of CH$_2$ at position 24); from 4.35 to 4.55 (mt, 1H: 1H of CH$_2$ at position 9); from 4.60 to 4.80 (mt, 2H: CH at position 3 and CH at position 27); from 4.80 to 4.90 (mt: CH at position 13 of the E isomer and CH at position 14 of the Z isomer); 5.06 (mt: CH at position 14 of the E isomer); 5.57 (d, J=9 Hz: CH at position 13 of the Z isomer); from 5.60 to 5.90 (mt, 2H: CH at position 10 and CH at position 6); 6.05 and 6.14 (2 d, J=16 Hz, 1H in total respectively CH at position 11 of the E isomer and CH at position 11 of the Z isomer); 6.28 (mt: CONH of the Z isomer); 6.47 (d, J=16 and 5 Hz, H: CH at position 5); 7.47 (mt: CONH of the E isomer); 7.77 (s: CH at position 20 of the E isomer); 8.08 (s: CH at position 20 of the Z isomer).

EXAMPLE 20

(16R)-16-Propyloxyamino-16-deoxopristinamycin II$_B$

By carrying out the procedure as in Example 17, but starting with 1.5 g of pristinamycin II$_B$ O-propyloxime (50/50 mixture of the Z and E isomers) in solution in 45 cm$^3$ of methanol, 15 cm$^3$ of acetic acid and 1.61 g of sodium cyanoborohydride and after 50 hours of reaction, 1.4 g of a white solid are isolated, which solid is purified by flash chromatography (eluent CH$_2$Cl$_2$—MeOH 97/3 by volume) to give 0.31 g of (16R)-16-propyloxyamino-16-deoxopristinamycin II$_B$ in the form of a white solid melting at 135 EC.

$^1$H NMR spectrum (400 MHz, CDCl$_3$, δ in ppm): from 0.90 to 1.05 (mt, 9H: CH$_3$ at position 30—CH$_3$ at position 31 and CH$_3$ of propyl); 1.08 (d, J=6.5 Hz, 3H: CH$_3$ at position 32); from 1.55 to 1.70 (mt, 3H: 1H of CH$_2$ at position 15 and central CH$_2$ of propyl); from 1.70 to 2.00 (mt, 5H: 1H of CH$_2$ at position 15—CH$_2$ at position 25—1H of CH$_2$ at position 26 and CH at position 29); 1.80 (s, 3H: CH$_3$ at position 33); 2.14 (mt, 1H: 1H of CH$_2$ at position 26); from 2.20 to 2.35 (broad unresolved complex, 1H: OH); from 2.70 to 2.80 (mt, 1H: CH at position 4); 2.75 (dd, J=16 and 8 Hz, 1H: 1H of CH$_2$ at position 17); 3.27 (dd, J=16 and 4 Hz, 1H: 1H of CH$_2$ at position 17); from 3.40 to 3.55 (mt, 2H: CH at position 16 and 1H of CH$_2$ at position 9); 3.69 (t, J=6.5 Hz, 2H: OCH$_2$); from 3.85 to 4.00 (mt, 2H: CH$_2$ at position 24); 4.43 (mt, 1H: 1H of CH$_2$ at position 9); from 4.65 to 4.80 (mt, 3H: CH at position 3—CH at position 14 and CH at position 27); 5.36 (d, J=9 Hz, 1H: CH at position 13); from 5.40 to 5.60 (broad unresolved complex, 1H NH);

5.70 (mt, 1H: CH at position 10); 5.80 (dd, J=16 and 1.5 Hz, 1H: CH at position 6); 6.14 (mt, 1H: CONH); 6.17 (d, J=16 Hz, 1H: CH at position 11); 6.51 (dd, J=16 and 5 Hz, 1H: CH at position 5); 8.08 (s, 1H: CH at position 20).

Pristinamycin $II_B$ O-propyloxime (85/15 mixture of the Z and E isomers) may be prepared by carrying out the procedure as in Example 17, but starting with 4 g of pristinamycin $II_B$, 2.6 g of O-propylhydroxylamine hydrochloride in 60 cm$^3$ of pyridine. After extraction and drying under reduced pressure (2.7 kPa) at 20 EC, a solid is obtained which is stirred in acetonitrile to give, after filtration of the precipitate, 2.75 g of pristinamycin $II_B$ O-propyloxime (85/15 mixture of the Z and E isomers) in the form of a white solid melting at 130–132 EC and which is used as it is for subsequent operations.

$^1$H NMR spectrum (400 MHz, CDCl$_3$, δ in ppm): from 0.90 to 1.10 (mt, 12H: CH$_3$ at position 30—CH$_3$ at position 31—CH$_3$ at position 32 and CH$_3$ of propyl); from 1.60 to 1.75 (mt, 2H: central CH$_2$ of propyl); 1.75 (s, 3H: CH$_3$ at position 33); from 1.75 to 2.00 (mt, 4H: CH$_2$ at position 25—1H of CH$_2$ at position 26 and CH at position 29); 2.15 (mt, 1H: 1H of CH$_2$ at position 26); 2.51 and 2.65 (2 dd, respectively J=17 and 6 Hz and J=17.5 and 5 Hz, 1H each: CH$_2$ at position 15); 2.74 (mt, 1H: CH at position 4); 3.20 (d, J=6 Hz, 1H: OH); 3.38 (mt, 1H: 1H of CH$_2$ at position 9); 3.65 (d, J=15 Hz, 1H: 1H of CH$_2$ at position 17); 3.74 (mt, 1H: 1H of CH$_2$ at position 24); from 3.95 to 4.10 (mt, 4H: 1H of CH$_2$ at position 24—1H of CH$_2$ at position 17 and OCH$_2$); 4.43 (mt, 1H 1H of CH$_2$ at position 9); 4.67 (dd, J=10 and 3 Hz, 1H: CH at position 27); 4.72 (broad d, J=10 Hz, 1H: CH at position 3); 4.83 (mt, 1H: CH at position 14); 5.55 (d, J=9 Hz, 1H: CH at position 13); 5.69 (mt, 1H: CH at position 10); 5.78 (dd, J=17 and 1.5 Hz, 1H: CH at position 6); 6.13 (d, J=16 Hz, 1H: CH at position 11); 6.26 (mt, 1H: CONH); 6.46 (dd, J=17 and 5 Hz, 1H: CH at position 5); 8.07 (s, 1H: CH at position 20).

EXAMPLE 21
(16R)-16-Methoxyamino-16-deoxopristinamycin $II_A$

This compound may be obtained by carrying out the procedure as in Example 17, but starting with 3 g of pristinamycin $II_A$ O-methyloxime (65/25 mixture of the Z and E isomers) in solution in 90 cm$^3$ of methanol, 30 cm$^3$ of acetic acid and 3.4 g of sodium cyanoborohydride and after one week of reaction at about 20 EC and one week of reaction at 30–33 EC. 3 g of a white solid are thus obtained, which solid is purified by flash chromatography (eluent CH$_2$Cl$_2$—MeOH 97/3 by volume) to give 0.36 g of (16R)-16-methoxyamino-16-deoxopristinamycin $II_A$ in the form of a white solid melting at 150 EC.

$^1$H NMR spectrum (400 MHz, CDCl$_3$, δ in ppm): from 0.90 to 1.05 (mt, 6H: CH$_3$ at position 30 and CH$_3$ at position 31); 1.13 (d, J=6.5 Hz, 3H: CH$_3$ at position 32); 1.59 (broad s, 1H: OH); from 1.65 to 1.85 (mt, 2H: CH$_2$ at position 15); 1.73 (s, 3H: CH$_3$ at position 33); 2.03 (mt, 1H: CH at position 29); from 2.60 to 2.85 (mt, 2H: CH at position 4 and 1H of CH$_2$ at position 25); 2.64 (dd, J=14 and 11 Hz, 1H: 1H of CH$_2$ at position 17); 2.85 (mt, 1H: 1H of CH$_2$ at position 25); 2.95 (mt, 1H: CH at position 16); 3.20 (dd, J=14 and 2.5 Hz, 1H: 1H of CH$_2$ at position 17); 3.60 (s, 3H: OCH$_3$); 3.81 (broad d, J=18 Hz, 1H: 1H of CH$_2$ at position 9); 4.22 (mt, 1H: 1H of CH$_2$ at position 24); from 4.30 to 4.55 (mt, 3H 1H of CH$_2$ at position 9—1H of CH$_2$ at position 24 and CH at position 14); 4.83 (d, J=9 Hz, 1H: CH at position 13); 4.96 (broad d, J=10 Hz, 1H: CH at position 3); 5.47 (broad s, 1H: NH); 5.65 (mt, 1H: CH at position 10); 5.90 (broad d, J=16 Hz, 1H: CH at position 11); 6.03 (broad d, J=17 Hz, 1H: CH at position 6); 6.14 (t, J=3 Hz, 1H: CH at position 26); 6.62 (dd, J=17 and 7 Hz, 1H: CH at position 5); 7.48 (mt, 1H: CONH); 7.87 (s, 1H: CH at position 20).

Pristinamycin $II_A$ O-methyloxime (65/35 mixture of the Z-and E isomers) may be obtained by carrying out the procedure as in Example 17, but starting with 8 g of pristinamycin $II_A$ and 1.43 g of methoxyamine hydrochloride in 80 cm$^3$ of pyridine. After evaporation of the pyridine under reduced pressure (2.7 kPa) at 45 EC, extraction, stirring of the product in 300 cm$^3$ of diethyl ether, filtration and washing with diethyl ether, 7.51 g of pristinamycin $II_A$ O-methyloxime (65/35 mixture of the Z and E isomers) are obtained after drying under reduced pressure (90 Pa) at 40 EC in the form of a white solid melting at around 204 EC and which is used as it is in subsequent operations.

EXAMPLE 22
(16R)-16-(1-Pyrrolidinyl)amino-16-deoxopristinamycin $II_B$

By carrying out the procedure as in Example 17, but starting with 3 g of pristinamycin $II_B$ in solution in 30 cm$^3$ of methanol, 9 g of magnesium sulphate, 1.6 cm$^3$ of triethylamine and 1.4 g of 1-aminopyrrolidine hydrochloride and after having added, after 18 hours of stirring, 0.43 g of sodium cyanoborohydride and 1.5 cm$^3$ of acetic acid, the reaction mixture is stirred for 4 hours and gives after treatment 3.5 g of a yellow powder which is purified by flash chromatography [eluent: dichloromethane-methanol-acetonitrile (90–5–5 by volume)]. A solid is thus obtained which is stirred in ethyl ether and separated by filtration to give 0.56 g of (16R)-16-(1-pyrrolidinyl)amino-16-deoxopristinamycin $II_B$ in the form of a beige powder melting at around 130 EC.

$^1$H NMR spectrum (400 MHz, CDCl$_3$, δ in ppm): 0.95 and 1.00 (2 d, J=6.5 Hz, 3H each: CH$_3$ at position 30 and CH$_3$ at position 31); 1.06 (d, J=6.5 Hz, 3H: CH$_3$ at position 32); 1.53 (mt, 1H: 1H of CH$_2$ at position 15); from 1.70 to 2.20 (mt, 10H 1H of CH$_2$ at position 15—CH$_2$ at position 25—CH$_2$ at position 26—CH at position 29 and 2 CH$_2$ of pyrrolidinyl); 1.83 (s, 3H CH$_3$ at position 33); from 2.70 to 2.90 (mt, 6H: CH at position 4—1H of CH$_2$ at position 17 and 2 CH$_2$N of pyrrolidinyl); 3.06 (dd, J=16 and 4 Hz, 1H: 1H of CH$_2$ at position 17); from 3.40 to 3.50 (mt, 2H: 1H of CH$_2$ at position 9 and CH at position 16); 3.82 and 3.97 (2 mts, 1H each: CH$_2$ at position 24); 4.37 (mt, 1H: 1H of CH$_2$ at position 9); 4.57 (mt, 1H: CH at position 14); 4.73 (dd, J=9 and 3 Hz, 1H: CH at position 27); 4.77 (dd, J=10 and 2 Hz, 1H: CH at position 3); 5.41 (d, J=9 Hz, 1H: CH at position 13); 5.68 (mt, 1H: CH at position 10); 5.78 (dd, J=17 and 2 Hz, 1H: CH at position 6); 6.01 (mt, 1H: CONH); 6.18 (d, J=16 Hz, 1H: CH at position 11); 6.50 (dd, J=17 and 5 Hz, 1H: CH at position 5); 8.10 (s, 1H: CH at position 20).

EXAMPLE 23
(16R)-16-Dimethylamino-16-deoxypristinamycin $II_F$ 0.069 cm$^3$ of methylamine (8 M in ethanol) and then 0.015 cm$^3$ of acetic acid are added at a temperature close to 20 EC, under an argon atmosphere, to 0.27 g of pristinamycin $II_F$ in solution in 7 cm$^3$ of anhydrous acetonitrile. The mixture is stirred for 17 hours at a temperature close to 20 EC and then 0.038 g of sodium cyanoborohydride and 0.13 cm$^3$ of acetic acid are added under an argon atmosphere. The mixture is stirred for 3 hours at a temperature close to 20 EC before a further addition of 0.1 cm$^3$ of acetic acid. The reaction mixture is again stirred for 7 hours at a temperature close to 20 EC. 0.9 g of paraformaldehyde is then added and the medium is kept stirred for 17 hours at a temperature close to 20 EC. The white suspension obtained is filtered and the filtrate concentrated to dryness under reduced pressure (2.7 kPa) at a temperature close to 30 EC. The residual thick oil is then taken up in 15 cm³ of ethyl acetate and in 3 cm³ of water. After stirring for 15 minutes, the pH of the solution obtained is adjusted first to 9 by addition of concentrated sodium hydroxide, and then to 11 by addition of 1.5 cm³ of 1 N sodium hydroxide. The mixture obtained is stirred for about one hour, separated after settling and the organic phase washed with twice 1 cm³ of water and then extracted three times with 1 N hydrochloric acid (10 cm³, 1 cm³ and 0.5 cm³ successively). The pooled acidic aqueous phases are washed with 3 cm³ of ether and then alkalinized to pH 10–11 by addition of concentrated sodium hydroxide. The aqueous phase obtained is extracted with twice 4 cm³ of dichloromethane and the organic phases are combined, washed with 2 cm³ of water, dried over magnesium sulphate, filtered on sintered glass and then concentrated to dryness under reduced pressure (2.7 kPa) at a temperature close to 30 EC to give a white solid. The latter is stirred in 5 cm³ of ether and then filtered and dried to-constant weight (90 Pa at 20 EC) to give 0.17 g of a white powder. The latter is purified by flash chromatography [eluent: dichloromethane-methanol-acetonitrile (92-4-4) to give 0.067 g of (16R)-16-dimethylamino-16-deoxypristinamycin $II_F$ in the form of a white solid melting at 132 EC.

$^1$H NMR-spectrum (400 MHz, CDCl₃, δ in ppm): from 0.90 to 1.00 (mt, 6H: CH₃ at position 30 and CH₃ of ethyl at position 29); 1.07 (d, J=6.5 Hz, 3H: CH₃ at position 32); 1.18 and 1.50 (2 mts, 1H each: CH₂ of ethyl at position 29); from 1.60 to 2.00 (mt, 6H: CH₂ at position 15—CH₂ at position 25—1H of CH₂ at position 26 and CH at position 29); 1.78 (s, 3H: CH₃ at position 33); 2.12 (mt, 1H of CH₂ at position 26); 2.37 (s, 6H: N (CH₃)₂); 2.62 and 2.99 (2 dd, respectively J=16 and 10 Hz and J=16 and 4 Hz, 1H each: CH₂ at position 17); 2.76 (mt, 1H: CH at position 4); 3.22 (mt, 1H: CH at position 16); 3.51 (mt, 1H 1H of CH₂,at position 9); 3.83 and 3.94 (2 mts, 1H each: CH₂ at position 24); 4.35 (mt, 1H: 1H of CH₂ at position 9); 4.67 (mt, 1H: CH at position 14); 4.75 (dd, J=9 and 2.5 Hz, 1H1 CH at position 27); 4.91 (dd, J=9.5 and 1.5 Hz, 1H: CH at position 3); 5.35 (d, J=9 Hz, 1H: CH at position 13); 5.66 (mt, 1H: CH at position 10); 5.80 (dd, J=16 and 1.5 Hz, 1H: CH at position 6); 6.02 (mt, 1H: CONH); 6.18 (d, J=16 Hz, 1H: CH at position 11); 6.54 (dd, J=16 and 5 Hz, 1H: CH at position 5); 8.07 (s, 1H: CH at position 20).

EXAMPLE 24

By carrying out the procedure in a manner analogous to the examples above, the following products are also prepared:

(16R)-16-(methoxy)(methyl)amino-16-deoxypristinamycin $II_B$ (16R)-16-(methoxy)(methyl)amino-16-deoxypristinamycin $II_A$ (16R)-16-(ethoxy)(methyl)amino-16-deoxypristinamycin $II_B$ (16R)-16-(ethoxy)(methyl)amino-16-deoxypristinamycin $II_A$ (16R)-16-(methyl)(propoxyl)amino-16-deoxypristinamycin $II_B$ (16R)-16-(methyl)(propoxyl)amino-16-deoxypristinamycin $II_A$ (16R)-16-(allyloxy)(methyl)amino-16-deoxypristinamycin $II_B$ (16R)-16-(allyloxy)(methyl)amino-16-deoxypristinamycin $II_A$ (16R)-16-(cyclopropyl)(methyl)amino-16-deoxypristinamycin $II_B$ (16R)-16-(cyclopropyl)(methyl)amino-16-deoxypristinamycin $II_A$ (16R)-16-(methyl)(propyn-2-yl)amino-16-deoxypristinamycin $II_B$ (16R)-16-(methyl) (propyn-2-yl)amino-16-deoxypristinamycin $II_A$ (16R)-16-(methyl)(1-pyrrolidinyl)amino-16-deoxypristinamycin $II_B$ The present invention also relates to the pharmaceutical compositions containing at least one streptogramin derivative according to the invention, in the pure state, combined with a group B streptogramin derivative, where appropriate in salt form, and/or in the form of a combination with one or more compatible and pharmaceutically acceptable diluents or adjuvants.

The compositions according to the invention may be used by the oral, parenteral, topical or rectal route or in the form of aerosols.

As solid compositions for oral administration, tablets, pills, gelatin capsules, powders or granules may be used. In these compositions, the active product according to the invention, generally in the form of a combination, is mixed with one or more inert diluents or adjuvants, such as sucrose, lactose or starch. These compositions may comprise substances other than diluents, for example a lubricant such as magnesium stearate or a coating intended for a controlled release.

As liquid compositions for oral administration, there may be used solutions which are pharmaceutically acceptable, suspensions, emulsions, syrups and elixirs containing inert diluents such as water or paraffin oil. These compositions may also comprise substances other than diluents, for example wetting, sweetening or flavouring products.

Compositions for parenteral administration may be emulsions or sterile solutions. As solvent or vehicle, there may be used propylene glycol, a polyethylene glycol, vegetable oils, in particular olive oil, or injectable organic esters, for example ethyl oleate. These compositions may also contain adjuvants, in particular wetting, isotonizing, emulsifying, dispersing and stabilizing agents.

Sterilization may be carried out in several ways, for example with the aid of a bacteriological filter, by irradiation or by heating. They may also be prepared in the form of sterile solid compositions which may be dissolved at the time of use in sterile water or any other injectable sterile medium.

Compositions for topical administration may be, for example, creams, ointments, lotions or aerosols.

Compositions for rectal administration are suppositories or rectal capsules which contain, in addition to the active ingredient, excipients such as cocoa butter, semisynthetic glycerides or polyethylene glycols.

The compositions may also be aerosols. For use in the form of liquid aerosols, the compositions may be stable sterile solutions or solid compositions which are dissolved at the time of use in apyrogenic sterile water, in saline or any other pharmaceutically acceptable vehicle. For use in the form of dry aerosols intended to be directly inhaled, the active ingredient is finely divided and combined with a water-soluble solid diluent or vehicle with a particle size distribution of 30 to 80 μm, for example dextran, mannitol or lactose.

In human therapy, the new streptogramin derivatives according to the invention are particularly useful in the treatment of infections of bacterial origin. The doses depend on the desired effect and the duration of treatment. The doctor will determine the dosage which he judges to be the most appropriate depending on the treatment, depending on the age, weight and degree of infection and other factors specific to the subject to be treated. Generally, the doses are between 1 and 3 g of active product in 2 or 3 doses per day orally for an adult.

The following example illustrates a composition according to the invention.

EXAMPLE

Tablets containing a dose of 250 mg of active ingredient and having the following composition are prepared according to the usual technique:

| | |
|---|---|
| (16R)-16-dimethylamino-16-deoxo-pristinamycin II$_A$ | 175 mg |
| pristinamycin I$_B$ | 75 mg |
| excipient: starch, hydrated silica, dextrin, gelatin, magnesium stearate: qs | 500 mg |

What is claimed is:

1. A group A streptogramin derivative chosen from group A streptogramin derivatives of formula (I), salts thereof, and mixtures of stereoisomers of any of the foregoing:

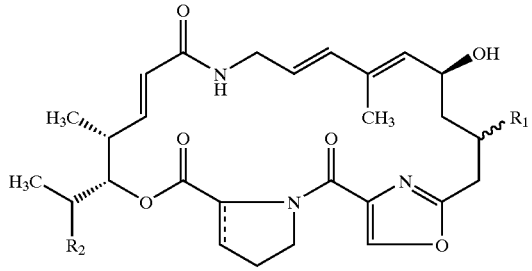

(I)

wherein:
R$_1$ is chosen from —NR'R" groups, wherein
    R' is chosen from a hydrogen atom and a methyl group, and
    R" is chosen from
        (i) a hydrogen atom,
        (ii) alkyl groups,
        (iii) cycloalkyl groups,
        (iv) an allyl group,
        (v) a propynyl group,
        (vi) a benzyl group,
        (vii) —OR'" groups, wherein R'" is chosen from a hydrogen atom, alkyl groups, cycloalkyl groups, an allyl group, a propynyl group, and a benzyl group, and
        (viii) —NR$_3$R$_4$ groups, wherein
            R$_3$ and R$_4$ are each a methyl group, or
            R$_3$ and R$_4$, which are identical or different, form, together with the nitrogen atom to which they are attached, a saturated or unsaturated 4- to 5-membered heterocyclyl group, wherein one of said members, in addition to said nitrogen atom, may be an atom chosen from an oxygen atom, a sulphur atom; and a nitrogen atom,
R$_2$ is chosen from a hydrogen atom, a methyl group, and an ethyl group,
the bond ══ is a single bond or a double bond,
unless otherwise stated, said alkyl groups are chosen from straight and branched C$_1$–C$_6$ alkyl groups,
unless otherwise stated, said cycloalkyl groups are chosen from C$_3$–C$_4$ cycloalkyl groups,
when said R" is chosen from a hydrogen atom, alkyl groups, cycloalkyl groups, an allyl group, a propynyl group, and a benzyl group:
    said group A streptogramin derivatives are chosen such that the carbon bearing said R$_1$ is of the R configuration,
    said salts are chosen such that the carbon bearing said R$_1$ is of the R configuration, and
    said mixtures are chosen such that said mixtures comprise at least one stereoisomer, wherein the carbon bearing said R$_1$ is of the R configuration, and at least one stereoisomer, wherein the carbon bearing said R$_1$ is of the S configuration, and wherein said R configuration is predominant, and
when R" is chosen from said —OR'" groups and said —NR$_3$R$_4$ groups:
    said group A streptogramin derivatives are chosen such that the carbon bearing said R$_1$ is of the R configuration or the S configuration,
    said salts are chosen such that the carbon bearing said R$_1$ is of the R configuration or the S configuration, and
    said mixtures are chosen such that said mixtures comprise at least one stereoisomer, wherein the carbon bearing said R$_1$ is of the R configuration, and at least one stereoisomer, wherein the carbon bearing said R$_1$ is of the S configuration.

2. A group A streptogramin derivative according to claim 1, wherein:
R$_1$ is chosen from —NR'R" groups, wherein
    R' is chosen from a hydrogen atom and a methyl group, and
    R" is chosen from
        (i) a hydrogen atom,
        (ii) alkyl groups,
        (iii) cycloalkyl groups,
        (iv) an allyl group,
        (v) a propynyl group,
        (vi) a benzyl group,
        (vii) —OR'" groups, wherein R'" is chosen from C$_1$–C$_6$ alkyl groups, an allyl group, and a propynyl group,
        (viii) —NR$_3$R$_4$ groups, wherein
            R$_3$ and R$_4$ are each a methyl group, or
            R$_3$ and R$_4$, which are identical or different, form, together with the nitrogen atom to which they are attached, a saturated or unsaturated 4- to 5-membered heterocyclyl group, wherein one of said members, in addition to said nitrogen atom, may be an atom chosen from an oxygen atom, a sulphur atom, and a nitrogen atom,
R$_2$ is chosen from a hydrogen atom, a methyl group, and an ethyl group,
the bond ══ is a single bond or a double bond,
when said R" is chosen from a hydrogen atom, alkyl groups, cycloalkyl groups, an allyl group, a propynyl group, and a benzyl group, said group A streptogramin derivatives and said salts thereof are chosen such that the carbon bearing said R$_1$ is of the R configuration and said mixtures comprise stereoisomers, wherein the carbon bearing R$_1$ is of the R configuration or the S configuration and wherein said R configuration is predominant, and
when R" is chosen from said —OR'" groups and said —NR$_3$R$_4$ groups, said group A streptogramin derivatives and said salts thereof are chosen such that the carbon bearing said $R_1$ is of the R configuration or the S configuration and said mixtures comprise stereoisomers, wherein the carbon bearing $R_1$ is of the R configuration or the S configuration.

3. A group A streptogramin derivative according to claim 1, wherein:

$R_1$ is chosen from —NR'R" groups, wherein
R' is chosen from a hydrogen atom and a methyl group, and
R" is chosen from
(i) a hydrogen atom,
(ii) $C_1$–$C_4$ alkyl groups,
(iii) cycloalkyl groups,
(iv) an allyl group,
(v) a propynyl group,
(vi) a benzyl group,
(vii) —OR'" groups, wherein R'" is chosen from $C_1$–$C_3$ alkyl groups, an allyl group, and a propynyl group,
(viii) —$NR_3R_4$ groups, wherein
$R_3$, and $R_4$, which are identical or different, form, together with the nitrogen atom to which they are attached, a 5-membered saturated heterocyclyl group, $R_2$ is chosen from a methyl group and an ethyl group,
the bond === is a single bond or a double bond,
when said R" is chosen from a hydrogen atom, alkyl groups, cycloalkyl groups, an allyl group, a propynyl group, and a benzyl group, said group A streptogramin derivatives and said salts thereof are chosen such that the carbon bearing said $R_1$ is of the R configuration and said mixtures comprise stereoisomers, wherein the carbon bearing $R_1$ is of the R configuration or the S configuration and wherein said R configuration is predominant, and
when R" is chosen from said —OR'" groups and said —$NR_3R_4$ groups, said group A streptogramin derivatives and said salts thereof are chosen such that the carbon bearing said $R_1$ is of the R configuration or the S configuration and said mixtures comprise stereoisomers, wherein the carbon bearing $R_1$ is of the R configuration or the S configuration.

4. A group A streptogramin derivative according to claim 1, wherein said group A streptogramin is (16R)-16-dimethylamino-16-deoxopristinamycin $II_A$ or a salt thereof:

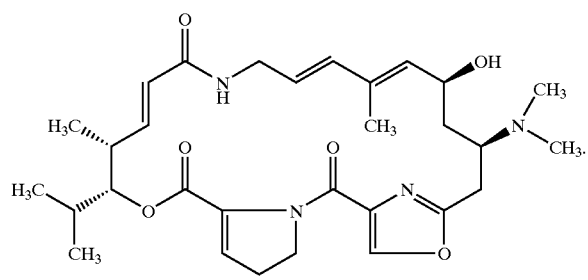

5. A group A streptogramin derivative according to claim 1, wherein said group A streptogramin is (16R)-16-methoxyamino-16-deoxopristinamycin $II_B$ or a salt thereof:

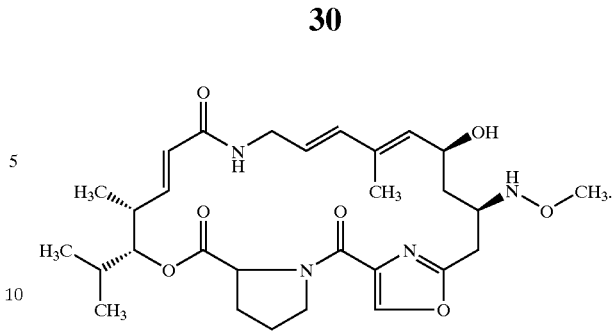

6. A group A streptogramin derivative according to claim 1, wherein said group A streptogramin is (16R)-16-ethoxyamino-16-deoxopristinamycin $II_B$ or a salt thereof:

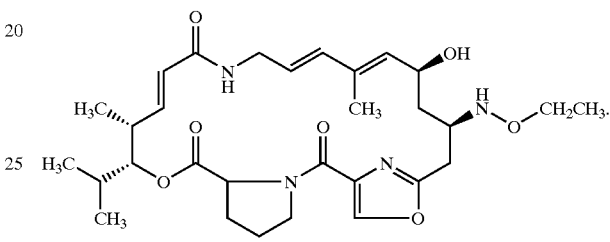

7. A group A streptogramin derivative according to claim 1, wherein said group A streptogramin is (16R)-16-allyloxyamino-16-deoxopristinamycin $II_B$ or a salt thereof:

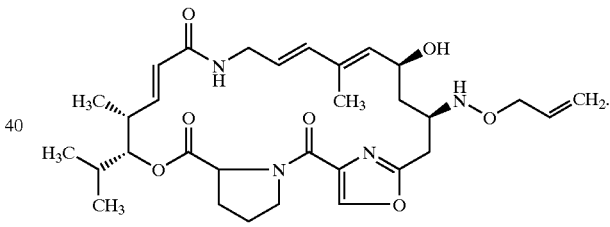

8. A group A streptogramin derivative according to claim 1, wherein said group A streptogramin is (16R)-16-methoxyamino-16-deoxopristinamycin $II_A$ or a salt thereof:

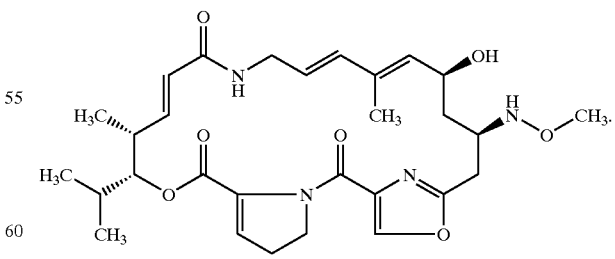

9. A process for preparing a group A streptogramin derivative according to claim 1, said process comprising:

(a) preparing a group A streptogramin derivative, wherein R' is a hydrogen atom, by reacting for a time and under conditions to form a group A streptogramin according to claim 1, in the presence of a reducing agent, an amine of formula (III):

  (III)

wherein R" is defined as in claim 1 with a natural pristinamycin of formula (II):

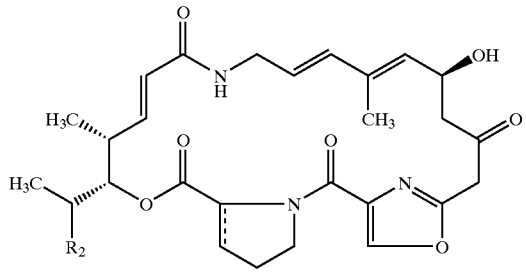  (II)

wherein $R_2$ is defined as in claim 1, (b) optionally reacting said group A streptogramin derivative of formula (I), wherein R' is a hydrogen atom, with formaldehyde or a formaldehyde derivative to generate formaldehyde in situ for a time and under conditions to form a second intermediate compound, and then reacting said second intermediate compound with a reducing agent for a time and under conditions to form a group A streptogramin derivative, wherein R' is a methyl group, and (c) optionally converting said group A streptogramin derivative of formula (I), prepared by (a) or (b) above, to a salt and separating said salt, wherein the carbon bearing said $R_1$ is of the R configuration, or optionally separating said group A streptogramin derivative, wherein the carbon bearing said $R_1$ is of the R configuration.

10. A process for preparing a group A streptogramin derivative according to claim 1, said process comprising:

(a) preparing an intermediate compound of formula (IV):

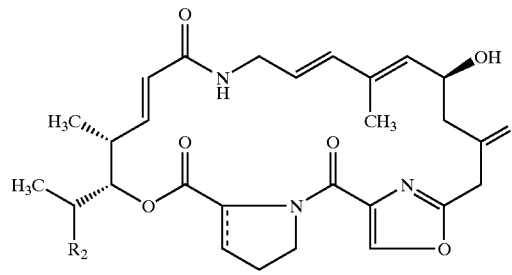  (IV)

wherein $R_2$ and R''' are defined as in claim 1 by reacting an amine of formula (III):

  (III)

wherein R" is chosen from —OR''' groups, and wherein said R''' groups are defined as in claim 1 with a natural pristinamycin of formula (II):

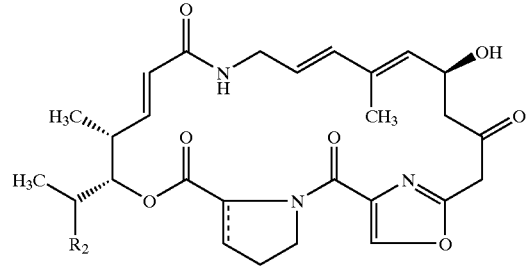  (II)

wherein $R_2$ is defined as in claim 1,
for a time and under conditions to form said intermediate compound of formula (IV), (b) isolating said intermediate compound of formula (IV), (c) reacting said isolated intermediate compound of formula (IV) with a reducing agent for a time and under conditions to form a group A streptogramin derivative of formula (I), wherein R' is a hydrogen atom, (d) optionally reacting said group A streptogramin derivative of formula (I), wherein R' is a hydrogen atom, with formaldehyde or a formaldehyde derivative to generate formaldehyde in situ for a time and under conditions to form a second intermediate compound, and then reacting said second intermediate compound with a reducing agent for a time and under conditions to form a group A streptogramin derivative of formula (I), wherein R' is a methyl group, and (e) optionally converting said group A streptogramin derivative of formula (I), prepared by (c) or (d) above, to a salt and/or separating its R-epimer.

11. A process for preparing a group A streptogramin derivative according to claim 1, said process comprising:

(a) preparing a group A streptogramin derivative, wherein R' is a hydrogen atom, by reacting, in the presence of a reducing agent:

(1) a ketone, chosen according to a desired R" group, wherein said R" is as defined in claim 1, with (2) an amine-containing derivative of formula (V):

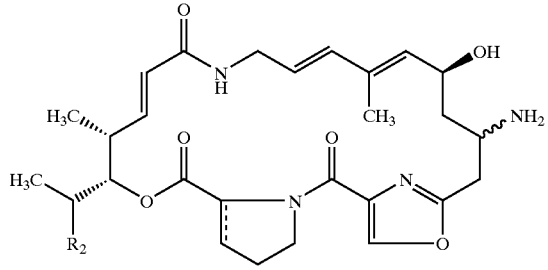  (V)

wherein $R_2$ is as defined in claim 1, (b) optionally reacting said group A streptogramin derivative of formula (I), wherein R' is a hydrogen atom, with formaldehyde or a formaldehyde derivative capable of generating formaldehyde in situ to form a second intermediate compound, and then reacting said second intermediate compound with a reducing agent to form a group A streptogramin derivative, wherein R' is a methyl group, and
(c) optionally converting said group A streptogramin derivative of formula (I), prepared by (a) or (b) above, to a salt and/or separating its R-epimer.

12. A composition comprising at least one group A streptogramin derivative of formula (I) or salt thereof according to claim 1 and at least one group B streptogramin derivative chosen from natural group B streptogramin components and semisynthetic group B streptogramin components.

13. A composition according to claim 12, wherein said at least one group B streptogramin derivative is chosen from pristinamycin $I_A$, pristinamycin $I_B$, pristinamycin $I_C$, pristinamycin $I_D$, pristinamycin $I_E$, pristinamycin $I_F$, pristinamycin $I_G$, virginiamycin $S_1$, virginiamycin $S_3$, virginiamycin $S_4$, vernamycin B, vernamycin C, and etamycin.

14. A composition according to claim 12, wherein said at least one group B streptogramin derivative is chosen from semisynthetic group B streptogramin derivatives of formula (A):

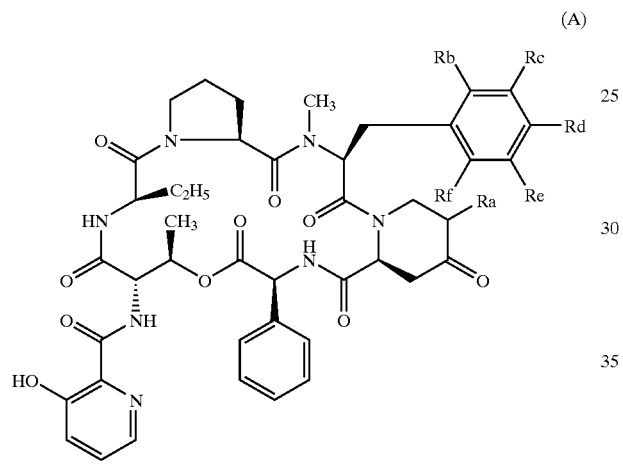

(A)

wherein:
(1) Rb, Rc, Re, and Rf are each a hydrogen atom;
Rd is chosen from a hydrogen atom and a dimethylamino group; and
Ra is chosen from:
(A) —CH$_2$R'a groups, wherein R'a is chosen from:
(i) a 3-pyrrolidinylthio group,
(ii) a 3-piperidylthio group,
(iii) a 4-piperidylthio group,
wherein said groups (i)–(iii) may be unsubstituted or substituted with at least one group chosen from alkyl groups, and
(iv) alkylthio groups which are substituted with 1 or 2 groups chosen from:
(a) a hydroxysulfonyl group,
(b) alkylamino groups,
(c) dialkylamino groups, which may be unsubstituted or substituted with at least one group chosen from a mercapto group or dialkylamino groups,
(d) a piperazine ring, a morpholino group, a thiomorpholino group, a piperdino group, a 1-pyrrolidinyl group, a 2-piperidyl group, a 3-piperidyl group, and a 4-piperidyl group, a 2-pyrrolidinyl group, and a 3-pyrrolidinyl group, each of which may be unsubstituted or substituted with alkyl, and (B) =CHR'a groups, wherein R'a is chosen from:
(i) a 3-pyrrolidinylamino group,
(ii) a 3-piperidylamino group and a 4-piperidylamino group,
(iii) a 3-pyrrolidinyloxy group,
(iv) a 3-piperidyloxy group and a 4-piperidyloxy group,
(v) a 3-pyrrolidinylthio group,
(vi) a 3-piperidylthio group and a 4-piperidylthio group,
wherein said groups (i)–(vi) may be unsubstituted or substituted with at least one group chosen from alkyl groups,
(vii) alkylamino groups,
(viii) alkyloxy groups, and
(ix) alkylthio groups which are substituted with 1 or 2 groups chosen from:
(a) a hydroxysulfonyl group,
(b) alkylamino groups,
(c) dialkylamino groups unsubstituted or substituted with at least one group chosen from dialkylamino groups,
(d) trialkylammonio groups,
(e) a 4-imidazolyl group, and a 5-imidazolyl group, each of which may be unsubstituted or substituted with alkyl,
(f) a piperazine ring, a morpholino group, a thiomorpholino group, a piperidino group, a 1-pyrrolidinyl group, a 2-piperidyl group, a 3-piperidyl group, a 4-piperidyl group, a 2-pyrrolidinyl group, and a 3-pyrrolidinyl group, each of which may be unsubstituted or substituted with alkyl,
(C) a 3-quinuclidinylthiomethyl group, and
(D) a 4-quinuclidinylthiomethyl group; or
(2) Ra is a hydrogen atom, and
(a) Rb, Re, and Rf are each a hydrogen atom, and Rd is chosen from a —NHCH$_3$ group and a —N(CH$_3$)$_2$ group, and Rc is chosen from a chlorine atom and a bromine atom, or when Rd is a —N(CH$_3$)$_2$ group, Rc is chosen from (C$_3$–C$_5$)alkenyl groups, or
(b) Rb, Rd, Re, and Rf are each a hydrogen atom, and Rc is chosen from halogen atoms, aminomonoalkyl groups, aminodialkyl groups, alkyloxy groups, a trifluoromethyloxy group, thioalkyl groups, (C$_1$–C$_3$) alkyl groups, and trihalomethyl groups, or
(c) Rb, Rc, Re, and Rf are each a hydrogen atom, and Rd is chosen from halogen atoms, an ethylamino group, a diethylamino group, a methylethylamino group, alkyloxy groups, a trifluoromethyloxy group, thioalkyl groups, (C$_1$–C$_6$) alkyl groups, aryl groups, and trihalomethyl groups, or
(d) Rb, Re, and Rf are each a hydrogen atom, Rc is chosen from halogen atoms, aminomonoalkyl groups, aminodialkyl groups, alkyloxy groups, a trifluoromethyloxy group, thioalkyl groups, and (C$_1$–C$_3$) alkyl groups, and Rd is chosen from halogen atoms, an amino group, aminomonoalkyl groups, aminodialkyl groups, alkyloxy groups, a trifluoromethyloxy group, thioalkyl groups, (C$_1$–C$_6$) alkyl groups, and trihalomethyl groups, or
(e) Rc, Re, and Rf are each a hydrogen atom, and Rb and Rd are each a methyl group.

15. A pharmaceutical composition comprising at least one group A streptogramin derivative of formula (I) or salt thereof according to claim 1 and at least one group B streptogramin derivative, wherein said composition optionally comprises at least one pharmaceutically acceptable diluent, at least one pharmaceutically acceptable adjuvant, or at least one pharmaceutically acceptable diluent and at least one pharmaceutically acceptable adjuvant.

16. A process for preparing a group A streptogramin derivatve according to claim 1, said process comprising:

(a) preparing a group A streptogramin derivative, wherein R' is a hydrogen atom, by reacting for a time and under conditions to form a group A streptogramin according to claim 1, in the presence of a reducing agent, an amine of formula (III):

$$H_2N-R'' \tag{III}$$

wherein R'' is defined as in claim 1 with a natural pristinamycin of formula (II):

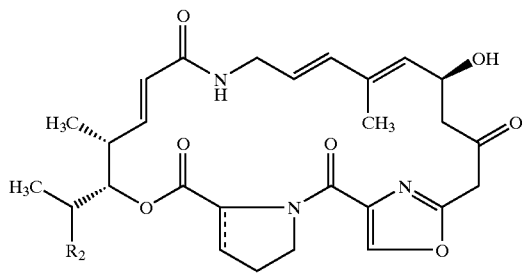

wherein $R_2$ is defined as in claim 1, (b) optionally reacting said group A streptogramin derivative of formula (I), wherein R' is a hydrogen atom, with formaldehyde or a formaldehyde derivative to generate formaldehyde in situ for a time and under conditions to form a second intermediate compound, and then reacting said second intermediate compound with a reducing agent for a time and under conditions to form a group A streptogramin derivative, wherein R' is a methyl group, (c) optionally converting said group A streptogramin derivative of formula (I), prepared by (a) or (b) above, to a salt and separating said salt, wherein the carbon bearing said $R_1$ is of the R configuration, or optionally separating said group A streptogramin derivative, wherein the carbon bearing said $R_1$ is of the R configuration, and (d) isolating said group A streptogramin derivative of formula (I) or salt thereof, prepared by (a), (b), or (c) above.

17. A process for preparing a group A streptogramin derivative according to claim 1, said process comprising:

(a) preparing an intermediate compound of formula (IV):

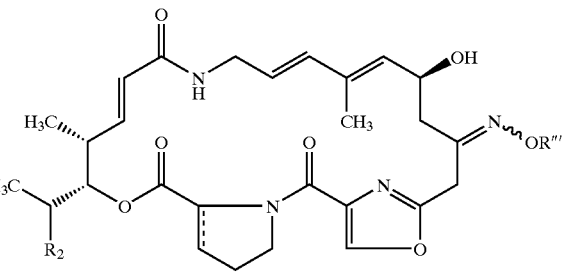

wherein $R_2$ and R''' are defined as in claim 1 by reacting an amine of formula (III):

$$H_2N-R'' \tag{III}$$

wherein R'' is chosen from —OR''' groups, and wherein said R''' groups are defined as in claim 1 with a natural pristinamycin of formula (II):

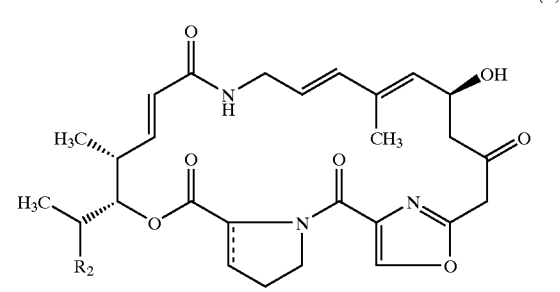

wherein $R_2$ is defined as in claim 1, for a time and under conditions to form said intermediate compound of formula (IV), (b) isolating said intermediate compound of formula (IV), (c) reacting said isolated intermediate compound of formula (IV) with a reducing agent for a time and under conditions to form a group A streptogramin derivative of formula (I), wherein R' is a hydrogen atom, (d) optionally reacting said group A streptogramin derivative of formula (I), wherein R' is a hydrogen atom, with formaldehyde or a formaldehyde derivative capable of generating formaldehyde in situ for a time and under conditions to form a second intermediate compound, and then reacting said second intermediate compound with a reducing agent for a time and under conditions to form a group A streptogramin derivative of formula (I), wherein R' is a methyl group, (e) optionally converting said group A streptogramin derivative of formula (I), prepared by (c) or (d) above, to a salt and/or separating its R-epimer, and (f) isolating said group A streptogramin derivative of formula (I) or salt thereof, prepared by (c), (d), or (e) above.

* * * * *